(12) United States Patent
Shaolian et al.

(10) Patent No.: US 6,660,030 B2
(45) Date of Patent: Dec. 9, 2003

(54) BIFURCATION GRAFT DEPLOYMENT CATHETER

(75) Inventors: Samuel M. Shaolian, Newport Beach, CA (US); Gilbert Madrid, Laguna Niguel, CA (US); Thanh Van Nguyen, Irvine, CA (US); Trinh Van Pham, Santa Ana, CA (US)

(73) Assignee: Endologix, Inc., Irvine, CA (US)

( * ) Notice: Subject to any disclaimer, the term of this patent is extended or adjusted under 35 U.S.C. 154(b) by 8 days.

(21) Appl. No.: 09/747,094

(22) Filed: Dec. 22, 2000

(65) Prior Publication Data

US 2001/0012943 A1 Aug. 9, 2001

Related U.S. Application Data

(63) Continuation-in-part of application No. 09/525,778, filed on Mar. 15, 2000, now Pat. No. 6,500,202, which is a continuation-in-part of application No. 09/251,363, filed on Feb. 17, 1999, now Pat. No. 6,197,049, which is a continuation-in-part of application No. 09/210,280, filed on Dec. 11, 1998, now Pat. No. 6,187,036.

(51) Int. Cl.[7] .................................................. A61F 2/06
(52) U.S. Cl. ..................................... 623/1.11; 623/1.23
(58) Field of Search ................................ 623/1.1, 1.11, 623/1.15, 1.35, 1.13, 1.16, 1.25; 606/198, 194, 153; 128/898

(56) References Cited

U.S. PATENT DOCUMENTS

| | | | |
|---|---|---|---|
| 2,127,903 A | 8/1938 | Bowen | |
| 2,437,542 A | 3/1948 | Krippendorf | |
| 2,845,959 A | 8/1958 | Sidebotham | |
| 2,990,605 A | 7/1961 | Demsyk | |

(List continued on next page.)

FOREIGN PATENT DOCUMENTS

| | | |
|---|---|---|
| DE | 295 21 548 U1 | 2/1995 |
| DE | 295 21 776 U1 | 2/1995 |
| EP | 458 568 A1 | 5/1991 |
| EP | 0 177 330 B1 | 6/1991 |
| EP | 282 175 B1 | 11/1991 |
| EP | 596 145 A1 | 10/1992 |
| EP | 621 015 A1 | 4/1993 |
| EP | 323 176 B1 | 3/1994 |
| EP | 0 596 145 A1 | 5/1994 |
| EP | 0 621 015 A1 | 10/1994 |
| EP | 782 841 A2 | 2/1995 |
| EP | 783 873 A2 | 2/1995 |
| EP | 783 874 A2 | 2/1995 |
| EP | 659 389 A1 | 6/1995 |
| EP | 0 659 389 A1 | 6/1995 |
| EP | 689 806 A2 | 1/1996 |
| EP | 747 020 A2 | 2/1996 |
| EP | 712 614 A1 | 5/1996 |
| EP | 732 088 A3 | 9/1996 |
| EP | 0 740 928 A2 | 11/1996 |

(List continued on next page.)

Primary Examiner—Corrine McDermott
Assistant Examiner—Crystal Gilpin
(74) Attorney, Agent, or Firm—Knobbe, Martens, Olson & Bear, LLP.

(57) ABSTRACT

Disclosed is a deployment catheter for deploying a tubular endoluminal vascular prosthesis, useful in treating, for example, an abdominal aortic aneurysm. The deployment catheter includes a proximal tubular section and a distal tubular section which are axially movable in opposite directions to deploy a prosthesis. A central core extends throughout the proximal tubular section and into the distal tubular section. A reinforcing structure is carried by the central core, spanning the junction between the proximal tubular section and distal tubular section, to improve flexibility characteristics of the catheter. In one embodiment, the proximal tubular section and/or distal tubular section are rotationally linked to the central core.

17 Claims, 14 Drawing Sheets

U.S. PATENT DOCUMENTS

| | | |
|---|---|---|
| 3,029,819 A | 4/1962 | Starks |
| 3,096,560 A | 7/1963 | Liebig |
| 3,805,301 A | 4/1974 | Liebig |
| 4,497,074 A | 2/1985 | Rey et al. |
| 4,501,263 A | 2/1985 | Harbuck |
| 4,503,568 A | 3/1985 | Madras |
| 4,592,754 A | 6/1986 | Gupte et al. |
| 4,617,932 A | 10/1986 | Kornberg |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,922,905 A | 5/1990 | Strecker |
| 4,981,478 A | 1/1991 | Evard et al. |
| 4,994,071 A | 2/1991 | MacGregor |
| 5,019,090 A | 5/1991 | Pinchuk |
| 5,064,435 A | 11/1991 | Porter |
| 5,078,726 A | 1/1992 | Kreamer |
| 5,104,399 A | 4/1992 | Lazarus |
| 5,108,424 A | 4/1992 | Hoffman, Jr. et al. |
| 5,123,917 A | 6/1992 | Lee |
| 5,133,732 A | 7/1992 | Wiktor |
| 5,135,536 A | 8/1992 | Hillstead |
| 5,156,619 A | 10/1992 | Ehrenfeld |
| 5,178,634 A | 1/1993 | Martinez |
| 5,197,976 A | 3/1993 | Herweck et al. |
| 5,201,757 A | 4/1993 | Heyn et al. |
| 5,256,141 A | 10/1993 | Gencheff et al. |
| 5,275,622 A | 1/1994 | Lazarus et al. |
| 5,282,824 A | 2/1994 | Gianturco |
| 5,282,860 A | 2/1994 | Matsuno et al. |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpiel |
| 5,330,500 A | 7/1994 | Song |
| 5,342,387 A | 8/1994 | Summers |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,387,235 A | 2/1995 | Chuter |
| 5,397,355 A | 3/1995 | Marin et al. |
| 5,405,377 A | 4/1995 | Cragg |
| 5,415,664 A * | 5/1995 | Pinchuk ............... 604/523 |
| 5,423,886 A | 6/1995 | Arru et al. |
| 5,425,765 A | 6/1995 | Tiefenbrun et al. |
| 5,443,498 A | 8/1995 | Fontaine |
| 5,443,500 A | 8/1995 | Sigwart |
| 5,456,713 A | 10/1995 | Chuter |
| 5,458,615 A | 10/1995 | Klemm et al. |
| 5,462,530 A | 10/1995 | Jang |
| 5,464,450 A | 11/1995 | Buscemi et al. |
| 5,484,444 A | 1/1996 | Braunschweiler et al. |
| 5,489,295 A | 2/1996 | Piplani et al. |
| 5,496,365 A | 3/1996 | Sgro |
| 5,507,767 A | 4/1996 | Maeda et al. |
| 5,507,769 A * | 4/1996 | Marin et al. ............... 604/104 |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,545,211 A | 8/1996 | An et al. |
| 5,554,118 A | 9/1996 | Jang |
| 5,554,181 A | 9/1996 | Das |
| 5,562,726 A | 10/1996 | Chuter |
| 5,562,728 A | 10/1996 | Lazarus et al. |
| 5,571,173 A | 11/1996 | Parodi |
| 5,575,816 A | 11/1996 | Rudnick et al. |
| 5,575,818 A | 11/1996 | Pinchuk |
| 5,578,072 A | 11/1996 | Barone et al. |
| 5,591,197 A | 1/1997 | Orth et al. |
| 5,591,198 A | 1/1997 | Boyle et al. |
| 5,591,229 A | 1/1997 | Parodi |
| 5,591,230 A | 1/1997 | Horn et al. |
| 5,593,417 A | 1/1997 | Rhodes |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,783 A | 5/1997 | Quiachon et et al. |
| 5,628,788 A | 5/1997 | Pinchuk |
| 5,630,829 A | 5/1997 | Lauterjung |
| 5,632,772 A | 5/1997 | Alcime et al. |
| 5,639,278 A | 6/1997 | Dereume et al. |
| 5,641,373 A | 6/1997 | Shannon et al. |
| 5,643,339 A | 7/1997 | Kavteladze et al. |
| 5,647,857 A | 7/1997 | Anderson et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,614 A | 9/1997 | Edoga |
| 5,662,700 A | 9/1997 | Lazarus |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,669,880 A | 9/1997 | Solar |
| 5,669,924 A | 9/1997 | Shaknovich |
| 5,674,241 A | 10/1997 | Bley et al. |
| 5,674,276 A | 10/1997 | Andersen et al. |
| 5,676,696 A | 10/1997 | Marcade |
| 5,676,697 A | 10/1997 | McDonald |
| 5,679,400 A | 10/1997 | Tuch |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,716,365 A | 2/1998 | Giocoechea et al. |
| 5,716,393 A | 2/1998 | Lindenberg et al. |
| 5,718,724 A | 2/1998 | Giocoechea et al. |
| 5,718,973 A | 2/1998 | Lewis et al. |
| 5,720,776 A | 2/1998 | Chuter et al. |
| 5,723,004 A | 3/1998 | Dereume et al. |
| 5,733,325 A | 3/1998 | Robinson et al. |
| 5,746,766 A | 5/1998 | Edoga |
| 5,749,880 A | 5/1998 | Banas et al. |
| 5,755,770 A | 5/1998 | Ravenscroft |
| 5,755,771 A | 5/1998 | Penn et al. |
| 5,769,885 A | 6/1998 | Quiachon et al. |
| 5,769,887 A | 6/1998 | Brown et al. |
| 5,782,909 A | 7/1998 | Quiachon et al. |
| 5,800,456 A | 9/1998 | Maeda et al. |
| 5,800,508 A | 9/1998 | Goicochea et al. |
| 5,810,836 A | 9/1998 | Hussein et al. |
| 5,824,037 A | 10/1998 | Fogarty et al. |

| | | |
|---|---|---|
| 5,824,039 A | 10/1998 | Piplani et al. |
| 5,824,053 A | 10/1998 | Khosravi et al. |
| 5,843,160 A | 12/1998 | Rhodes |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,860,998 A | 1/1999 | Robinson et al. |
| 5,868,783 A | 2/1999 | Tower |
| 5,879,321 A | 3/1999 | Hill |
| 5,879,366 A | 3/1999 | Shaw et al. |
| 5,891,193 A | 4/1999 | Robinson et al. |
| 5,893,887 A | 4/1999 | Jayaraman |
| 5,902,334 A | 5/1999 | Dwyer et al. |
| 5,906,640 A | 5/1999 | Penn et al. |
| 5,916,263 A | 6/1999 | Goicoceha et al. |
| 5,919,225 A | 7/1999 | Lau et al. |
| 5,925,075 A | 7/1999 | Myers et al. |
| 5,928,279 A | 7/1999 | Shannon et al. |
| 5,935,161 A | 8/1999 | Robinson et al. |
| 5,938,696 A | 8/1999 | Goicoechea et al. |
| 5,948,018 A | 9/1999 | Dereume et al. |
| 5,957,973 A | 9/1999 | Quiachon et al. |
| 5,961,546 A | 10/1999 | Robinson et al. |
| 5,961,548 A | 10/1999 | Shmulewitz |
| 6,004,347 A | 12/1999 | McNamara et al. |
| 6,004,348 A | 12/1999 | Banas et al. |
| 6,017,363 A | 1/2000 | Hojeibane |
| 6,027,779 A | 2/2000 | Campbell et al. |
| 6,027,811 A | 2/2000 | Campbell et al. |
| 6,030,415 A | 2/2000 | Chuter |
| 6,039,749 A | 3/2000 | Marin et al. |
| 6,039,755 A | 3/2000 | Edwin et al. |
| 6,039,758 A | 3/2000 | Quiachon et al. |
| 6,051,020 A | 4/2000 | Goicoechea et al. |
| 6,070,589 A | 6/2000 | Keith et al. |
| 6,074,398 A | 6/2000 | Leschinsky |
| 6,077,296 A | 6/2000 | Shokooji et al. |
| 6,077,297 A | 6/2000 | Robinson et al. |
| 6,106,548 A | 8/2000 | Reubin et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,168,610 B1 | 1/2001 | Marin et al. |
| 6,183,481 B1 | 2/2001 | Lee et al. |
| 6,187,036 B1 | 2/2001 | Shaolian et al. |
| 6,192,944 B1 | 2/2001 | Greenhalgh |
| 6,203,735 B1 | 3/2001 | Edwin et al. |
| 6,273,909 B1 | 8/2001 | Kugler et al. |
| 6,280,466 B1 | 8/2001 | Kugler et al. |
| 6,280,467 B1 | 8/2001 | Leonhardt |
| 6,283,991 B1 | 9/2001 | Cox et al. |

FOREIGN PATENT DOCUMENTS

| | | |
|---|---|---|
| EP | 740 928 A2 | 11/1996 |
| EP | 0 747 020 A2 | 12/1996 |
| EP | 732 089 A3 | 2/1997 |
| EP | 775 470 A1 | 5/1997 |
| EP | 0 775 470 A1 | 5/1997 |
| EP | 880 948 A1 | 5/1998 |
| EP | 880 938 A1 | 12/1998 |
| EP | 0 904 745 A2 | 3/1999 |
| EP | 974 314 A2 | 1/2000 |
| EP | 732 088 B1 | 4/2000 |
| ES | 1 038 606 | 7/1998 |
| JP | 9-511160 | 11/1997 |
| WO | WO 93/13825 | 1/1993 |
| WO | WO 93/13825 | 7/1993 |
| WO | WO 94/24961 | 2/1994 |
| WO | WO95/21592 | 2/1995 |
| WO | WO 96/41589 | 6/1996 |
| WO | WO 96/41589 | 12/1996 |
| WO | WO97/26936 | 1/1997 |
| WO | WO 97/10757 | 3/1997 |
| WO | WO 97/10777 | 3/1997 |
| WO | WO 97/14375 | 4/1997 |
| WO | WO 97/19652 | 6/1997 |
| WO | WO 98/02100 | 1/1998 |
| WO | WO 99/44536 | 9/1999 |
| WO | WO 99/47077 | 9/1999 |
| WO | WO 99/58084 | 11/1999 |

* cited by examiner

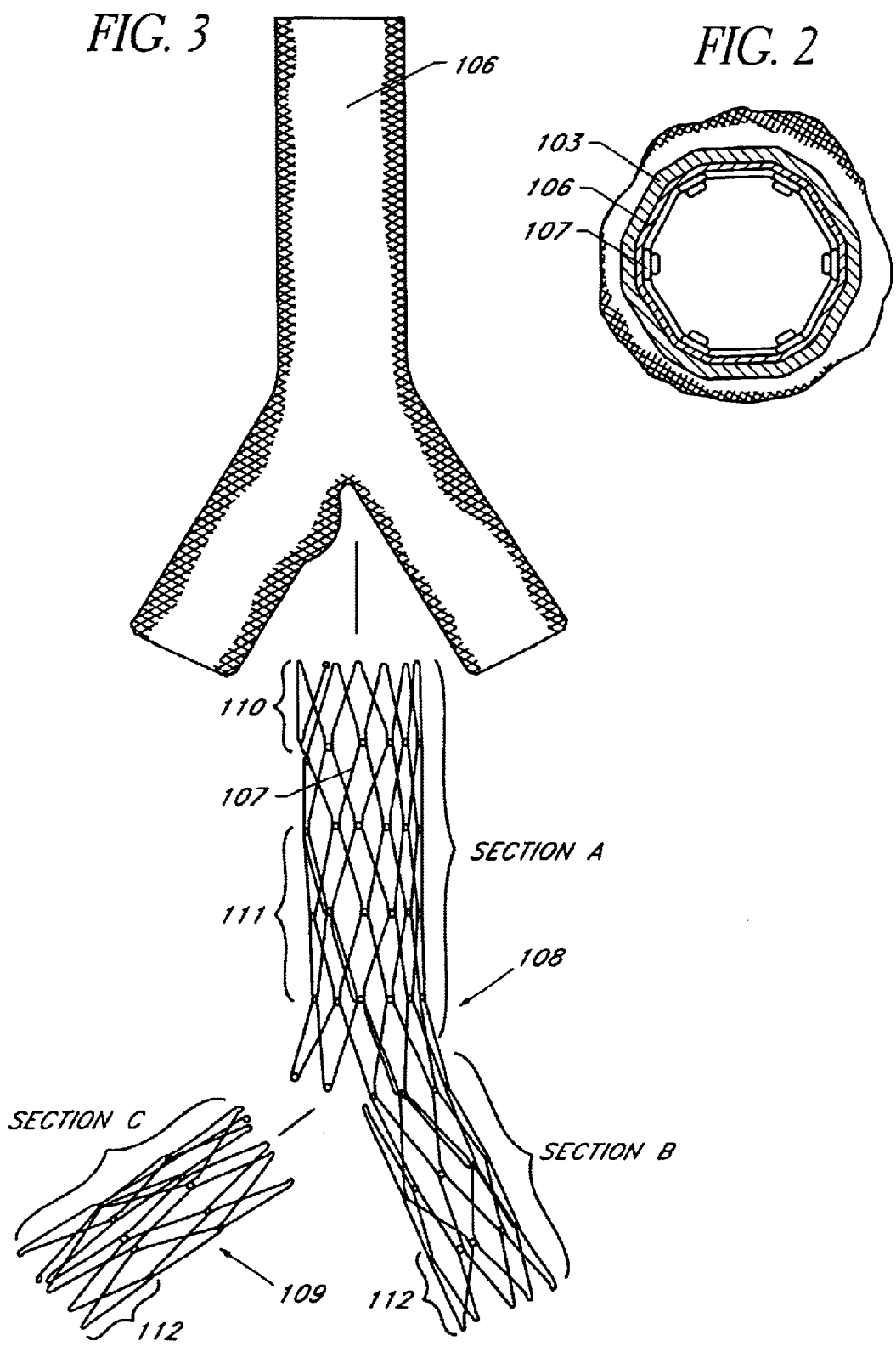

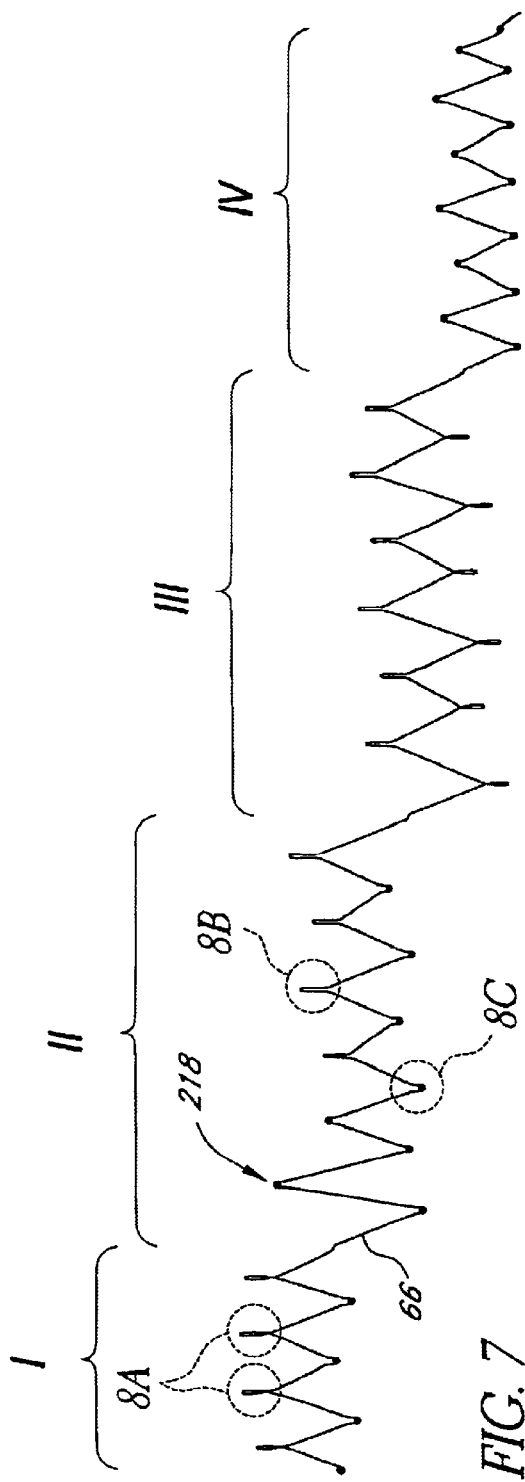
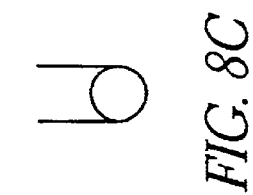
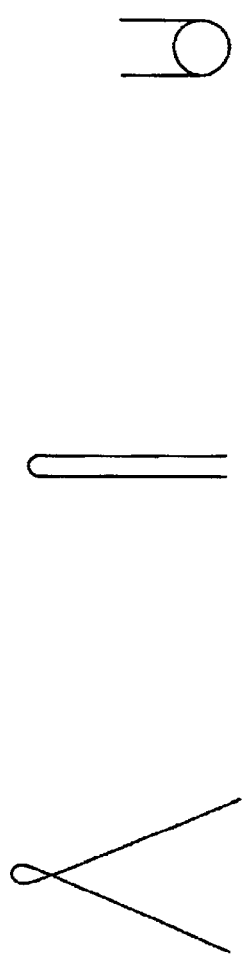
FIG. 7
FIG. 8A
FIG. 8B
FIG. 8C

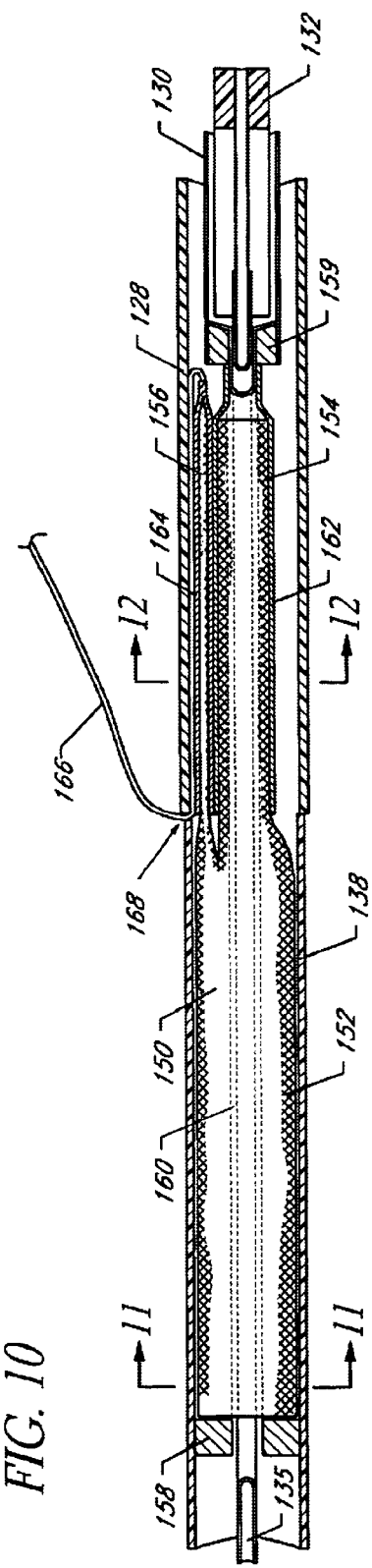
FIG. 10
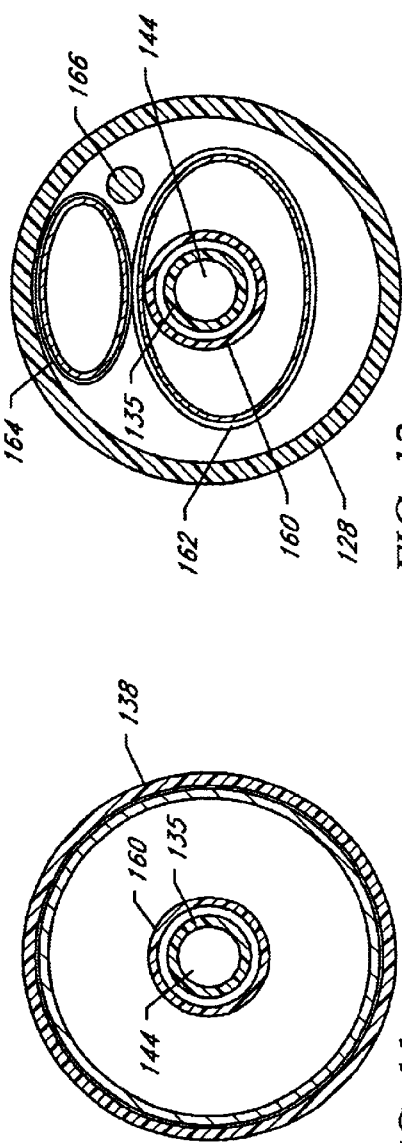
FIG. 12
FIG. 11

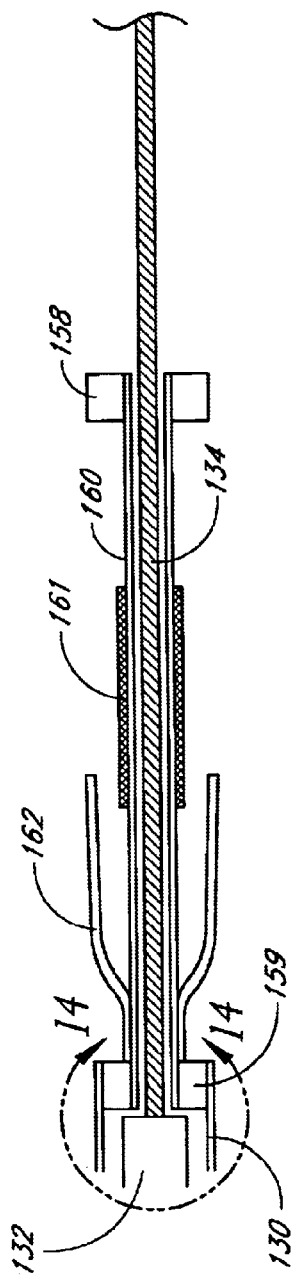
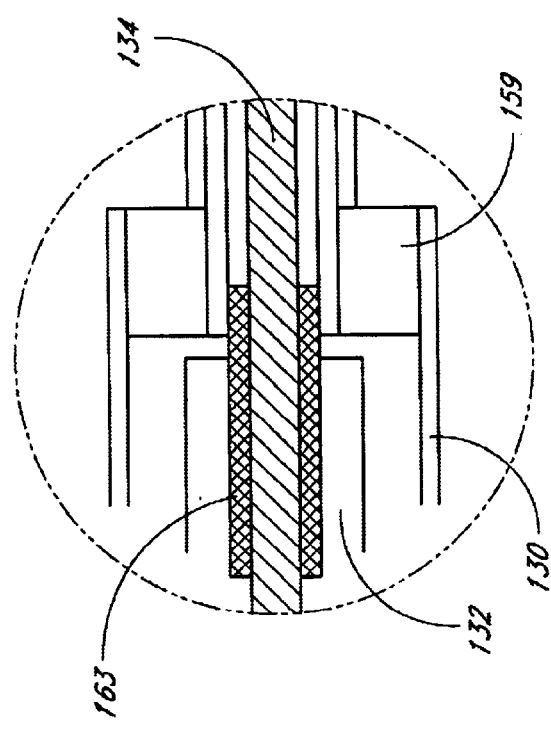
FIG. 13
FIG. 14

BIFURCATION GRAFT DEPLOYMENT CATHETER

This is a continuation-in-part of Ser. No. 09/525,778 filed on Mar. 15, 2000 now U.S. Pat. No. 6,500,202 which is a continuation-in-part of Ser. No. 09/251,363, filed Feb. 17, 1999 now U.S. Pat. No. 6,197,049, which is a continuation-in-part of Ser. No. 09/210,280, filed Dec. 11, 1998, now U.S. Patent No. 6,187,036 the disclosures of each of which are incorporated in their entireties herein by reference.

BACKGROUND OF THE INVENTION

The present invention relates to endoluminal vascular prosthesis deployment catheters, and in particular, to a deployment catheter for self-expanding straight segment or bifurcated prostheses for use in the treatment of abdominal aortic aneurysms.

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON®, TEFLON®, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. The graft must be secured, or sutured, to the remaining portion of the aorta, which may be difficult to perform because of the thrombosis present on the remaining portion of the aorta. Moreover, the remaining portion of the aorta wall is frequently friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft within the lumen of the artery.

In general, transluminally implantable prostheses adapted for use in the abdominal aorta comprise a tubular wire cage surrounded by a tubular PTFE or Dacron sleeve. Both balloon expandable and self expandable support structures have been proposed. Endovascular grafts adapted to treat both straight segment and bifurcation aneurysms have also been proposed.

Notwithstanding the foregoing, there remains a need for a structurally simple, easily deployable transluminally implantable endovascular prosthesis, with a support structure adaptable to span either a straight or bifurcated abdominal aortic aneurysm. Preferably, the tubular prosthesis can be self expanded at the site to treat the abdominal aortic aneurysm, and exhibits flexibility to accommodate nonlinear anatomies and normal anatomical movement.

SUMMARY OF THE INVENTION

There is provided in accordance with one aspect of the present invention, an endoluminal graft deployment catheter. The catheter comprises a proximal outer tube section, having a proximal end and a distal end, and an intermediate tube extending through the proximal tube section and beyond the distal end. A central core extends through the intermediate tube, and a cap is attached to the central core. The central core is rotationally linked to the intermediate tube.

Preferably, the intermediate tube is rotationally linked to the outer tube. The cap is axially movable between a first position in which it contacts the outer tube and a second position in which it is spaced distally apart from the outer tube, such as to deploy an entrapped prosthesis.

The central core preferably comprises a flexible tube. In one embodiment, the tube comprises a polymeric braid. One suitable polymer is polyimide.

In accordance with a further aspect of the present invention, the central core further comprises a reinforcing element which overlaps the point of contact between the cap and the outer tube. In one embodiment, the reinforcing element comprises a tubular structure carried by the flexible central core.

In accordance with a further aspect of the present invention, there is provided an endoluminal graft deployment catheter. The catheter comprises an elongate flexible body, having a proximal end and a distal end. A proximal outer tube section has a proximal end and a distal end, and a distal outer tube section has a proximal end and a distal end. The proximal outer tube section is rotationally linked to the distal outer tube section, and a central core extends through the proximal end distal outer tube sections. The proximal and distal tube sections define a prosthesis cavity therein for carrying a prosthesis, and axial separation of the proximal tube section from the distal tube section opens the cavity to release the prosthesis.

In one embodiment, each of the proximal tube section and distal tube section is rotationally linked to the central core. At least one of the proximal tube section and distal tube section is axially movable between a first position in which the cavity is closed and a second position in which the cavity is open. The proximal tube section and distal tube section thus form a junction when in the first position, and the catheter preferably further comprises a reinforcing element which spans the junction. In one embodiment, the reinforcing element comprises a tube for surrounding the central core.

Further features and advantages of the present invention will become apparent to those of ordinary skill in the art in view of the disclosure herein, when considered together with the attached drawings and claims.

BRIEF DESCRIPTION OF THE DRAWINGS

FIG. 2 is a cross-sectional view of the implanted graft taken along the lines 2—2 of FIG. 1.

FIG. 3 is an exploded view of the bifurcated vascular prosthesis in accordance with the present invention, showing a two-part self expandable wire support structure separated from an outer tubular sleeve.

FIG. 7 is a plan view of formed wire useful for rolling about an axis to form a branch support structure in accordance with the three-part support embodiment of the present invention shown in FIG. 5.

FIGS. 8A, 8B and 8C are enlargements of the apexes delineated by lines A, B and C, respectively, in FIG. 7.

FIG. 10 is an enlargement of the portion delineated by the line 10—10 in FIG. 9.

FIG. 11 is a cross-section taken along the line 11—11 in FIG. 10.

FIG. 12 is a cross-section taken along the line 12—12 in FIG. 10.

FIG. 13 is a fragmentary side elevational view of an enhanced flexibility embodiment of the present invention.

FIG. 14 is a enlarged detail view taken along the line 14—14 in FIG. 13.

DETAILED DESCRIPTION OF THE PREFERRED EMBODIMENT

Figure 1:
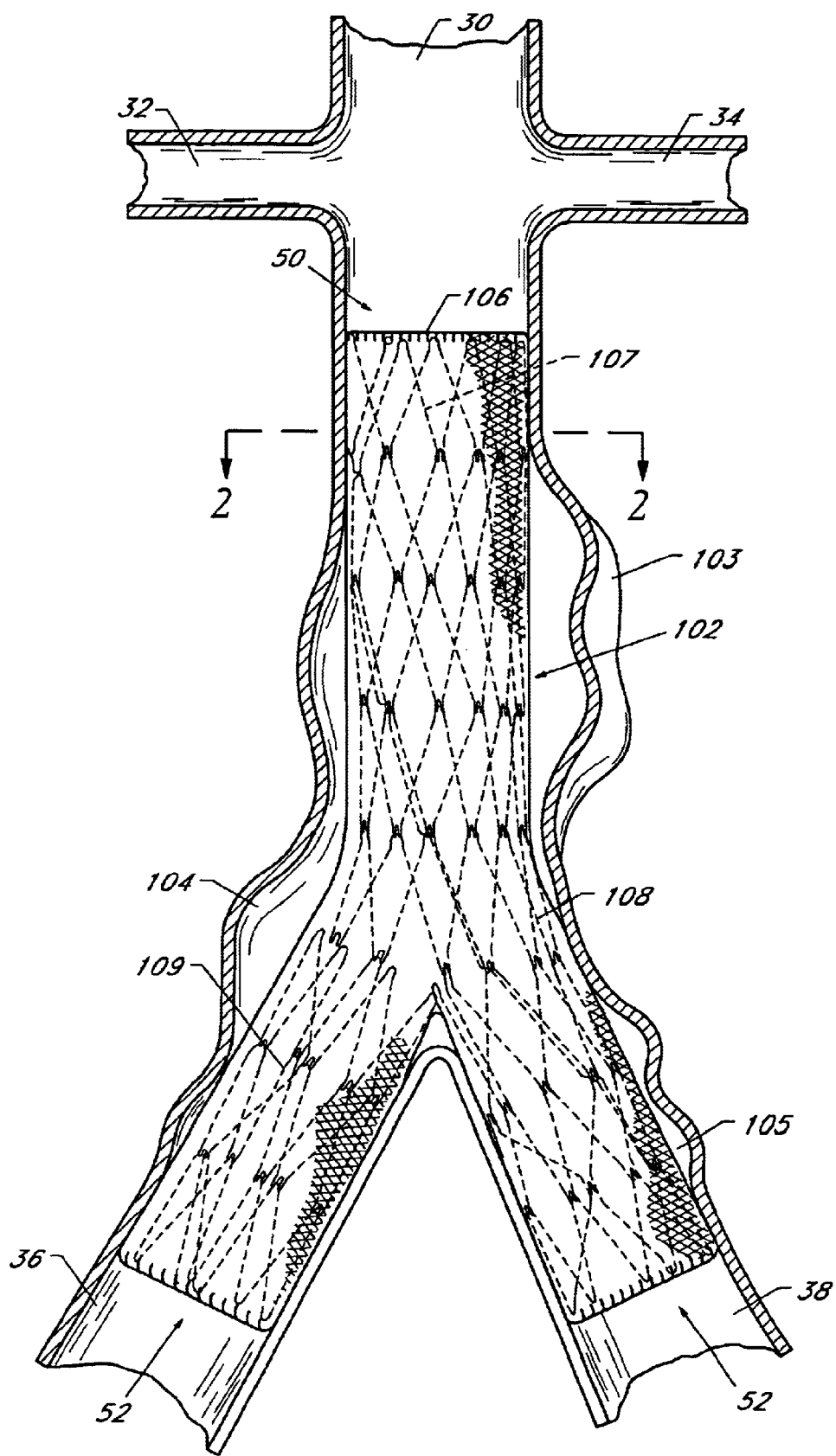
FIG. 1 is a schematic representation of a bifurcated vascular prosthesis in accordance with the present invention, positioned at the bifurcation between the abdominal aorta and the right and left common iliac arteries.

Referring to FIG. 1, there is disclosed a schematic representation of the abdominal part of the aorta and its principal branches. In particular, the abdominal aorta 30 is characterized by a right renal artery 32 and left renal artery 34. The large terminal branches of the aorta are the right and left common iliac arteries 36 and 38. Additional vessels (e.g., second lumbar, testicular, inferior mesenteric, middle sacral) have been omitted for simplification.

An expanded bifurcated endoluminal vascular prosthesis 102, in accordance with one aspect of the present invention, is illustrated spanning aneurysms 103, 104 and 105. Although certain prosthesis configurations are disclosed herein, these are only examples of prostheses which are deployable using the deployment catheter of the present invention. The deployment catheter may be used to deploy essentially any self expandable bifurcated or straight segment prosthesis, as will be apparent to those of skill in the art in view of the disclosure herein.

The endoluminal vascular prosthesis 102 includes a polymeric sleeve 106 and a tubular wire support 107, illustrated in situ in FIG. 1. The sleeve 106 and wire support 107 are more readily visualized in the exploded view shown in FIG. 3. The endoluminal prosthesis 102 illustrated and described herein depicts an embodiment in which the polymeric sleeve 106 is situated concentrically outside of the tubular wire support 107. However, other embodiments may include a sleeve situated instead concentrically inside the wire support or on both of the inside and the outside of the wire support. Alternatively, the wire support may be embedded within a polymeric matrix or layer which makes up the sleeve. Regardless of whether the sleeve 106 is inside or outside the wire support 107, the sleeve may be attached to the wire support by any of a variety of means, as has been previously discussed.

The tubular wire support 107 comprises a primary component 108 for traversing the aorta and a first iliac, and a branch component 109 for extending into the second iliac. The primary component 108 may be formed from a continuous single length of wire, throughout both the aorta trunk portion and the iliac branch portion. See FIGS. 3 and 4. Alternatively, each iliac branch component can be formed separately from the aorta trunk portion. Construction of the graft from a three part cage conveniently facilitates the use of different gauge wire in the different components (e.g. 0.014" diameter main trunk and 0.012" diameter branch components).

Figure 4:
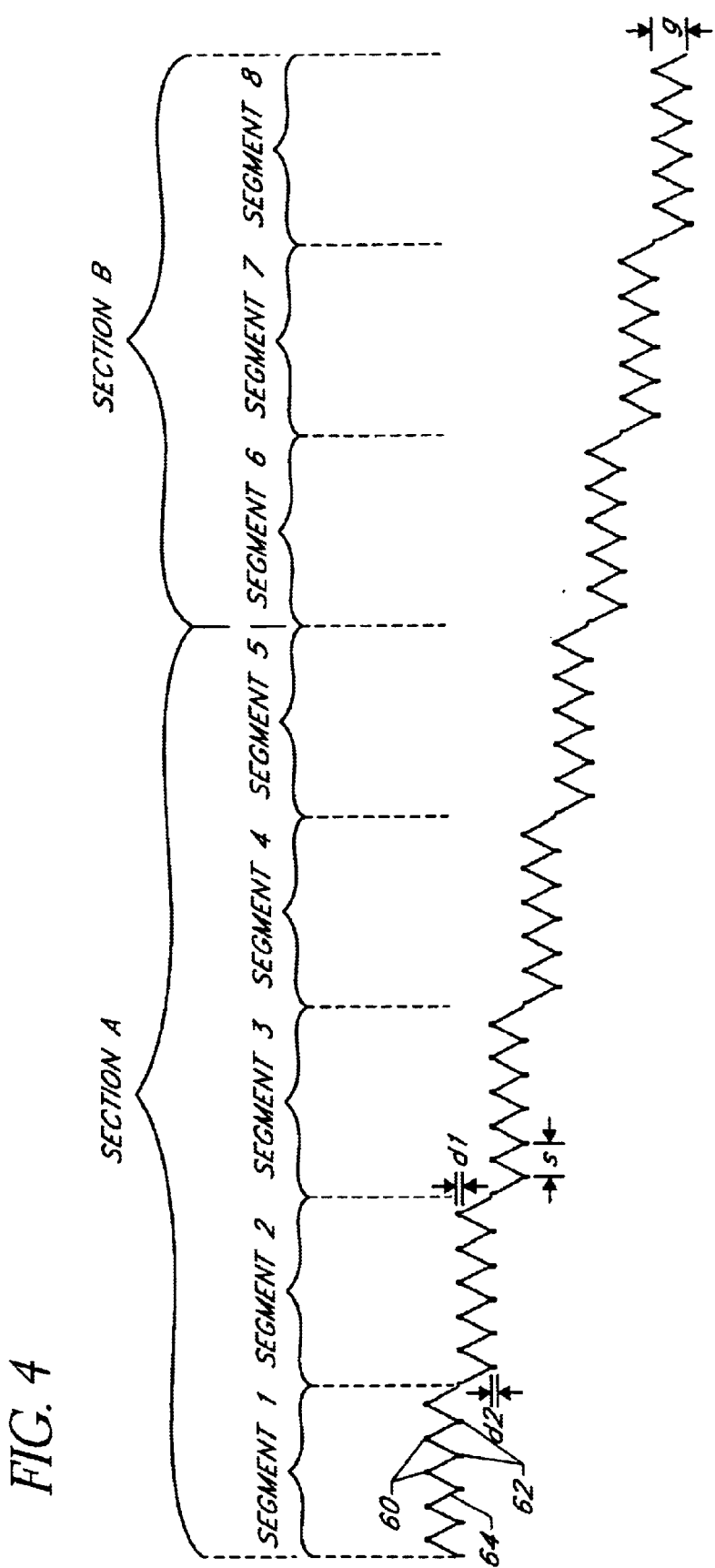
FIG. 4 is a plan view of formed wire useful for rolling about an axis into an aortic trunk segment and a first iliac branch segment support structure in accordance with the present invention.

The wire support 107 is preferably formed in a plurality of discrete segments, connected together and oriented about a common axis. In FIG. 4, Section A corresponds to the aorta trunk portion of the primary component 108, and includes segments 1–5. Segments 6–8 (Section B) correspond to the iliac branch portion of the primary component 108.

In general, each of the components of the tubular wire support 107 can be varied considerably in diameter, length, and expansion coefficient, depending upon the intended application. For implantation within a typical adult, the aorta trunk portion (section A) of primary component 108 will have a length within the range of from about 5 cm to about 12 cm, and, typically within the range of from about 9 cm to about 10 cm. The unconstrained outside expanded diameter of the section A portion of the primary component 108 will typically be within the range of from about 20 mm to about 40 mm. The unconstrained expanded outside diameter of the section A portion of primary component 108 can be constant or substantially constant throughout the length of section A, or can be tapered from a relatively larger diameter at the proximal end to a relatively smaller diameter at the bifurcation. In general, the diameter of the distal end of section A will be on the order of no more than about 95% and, preferably, no more than about 85% of the diameter of the proximal end of section A.

The right and left iliac portions, corresponding to section B on primary component 108 and section C will typically be bilaterally symmetrical. Section C length will generally be within the range of from about 1 cm to about 5 cm, and section C diameter will typically be within the range of from about 10 mm to about 20 mm.

Referring to FIG. 3, the wire cage 107 is dividable into a proximal zone 110, a central zone 111 and a distal zone 112. In addition, the wire cage 107 can have a transitional tapered and or stepped diameter within a given zone. Further details of the bifurcated and straight segment grafts in accordance with the present invention are disclosed in copending U.S. patent application Ser. No. 09/251,363 filed Feb. 17, 1999 and entitled Articulated Bifurcation Graft, the disclosure of which is incorporated in its entirety herein by reference.

Referring to FIG. 4, there is illustrated a plan view of the single formed wire used for rolling about a longitudinal axis to produce a primary segment 108 having a five segment aorta section and a three segment iliac section. The formed wire exhibits distinct segments, each corresponding to an individual tubular segment in the tubular support. Additional details of the wire cage layout and construction can be found in copending U.S. patent application Ser. No. 09/034,689 entitled Endoluminal Vascular Prosthesis, filed Mar. 4, 1998, the disclosure of which is incorporated in its entirety herein by reference.

Each segment has a repeating pattern of proximal bends 60 connected to corresponding distal bends 62 by wall sections 64 which extend in a generally zig-zag configuration when the segment is radially expanded. Each segment is connected to the adjacent segment through a connector 66, and one or more links 70 (see FIG. 6). The connector 66 in the illustrated embodiment comprises two wall sections 64 which connect a proximal bend 60 on a first segment with a distal bend 62 on a second, adjacent segment. The connector 66 may additionally be provided with a connector bend 68, which may be used to impart increased radial strength to the graft and/or provide a tie site for a circumferentially extending suture.

In the illustrated embodiment, section A is intended for deployment within the aorta whereas section B is intended to be deployed within a first iliac. Thus, section B will preferably have a smaller expanded diameter than section A. This may be accomplished by providing fewer proximal and distal bends 60, 62 per segment in section B or in other manners as will be apparent to those of skill in the art in view of the disclosure herein. In the illustrated embodiment, section B has one fewer proximal bend 60 per segment than does each segment in section A. This facilitates wrapping of the wire into a tubular prosthesis cage such as that illustrated in FIG. 3, so that the iliac branch has a smaller diameter than the aorta branch. At the bifurcation, an opening remains for connection of the second iliac branch. The second branch is preferably formed from a section of wire in accordance with the general principles discussed above, and in a manner that produces a similarly dimensioned wire cage as that produced by section B. The second iliac branch (section C) may be attached at the bifurcation to section A and/or section B in any of a variety of manners, to provide a secure junction therebetween. In one embodiment, one or two of the proximal bends 60 on section C will be secured to the corresponding distal bends 62 on the distal most segment of section A. Attachment may be accomplished such as through the use of a circumferentially threaded suture, through links 70 as has been discussed previously, through soldering or other attachment means. The attachment means will be influenced by the desired flexibility of the graft at the bifurcation, which will in turn be influenced by the method of deployment of the vascular graft as will be apparent to those of skill in the art in view of the disclosure herein.

Figure 5:
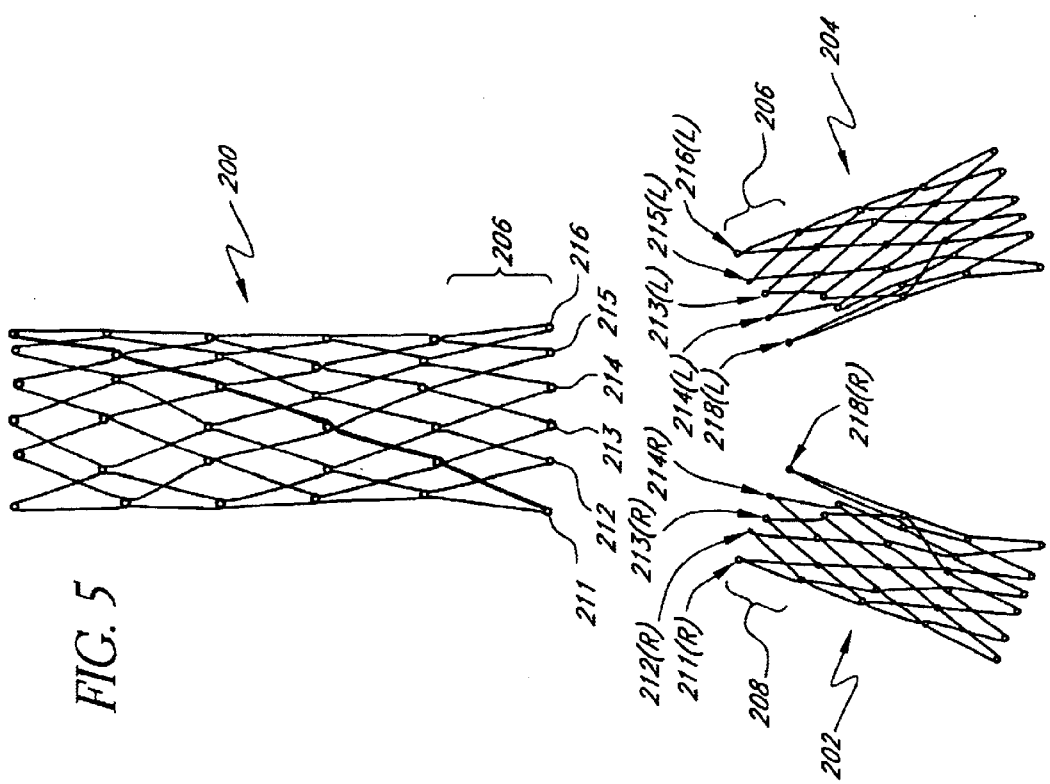
FIG. 5 is a schematic representation of another embodiment of the wire support structure for the bifurcated vascular prosthesis of the present invention, showing a main body support structure and separate branch support structures.

Referring to FIG. 5, there is disclosed an exploded schematic representation of a hinged or articulated variation in the tubular wire support structure for a bifurcated graft in accordance with present invention. The tubular wire support comprises a main body, or aortic trunk portion 200 and right 202 and left 204 iliac branch portions. Right and left designations correspond to the anatomic designations of right and left common iliac arteries. The proximal end 206 of the aortic trunk portion 200 has apexes 211–216 adapted for connection with the complementary apexes on the distal ends 208 and 210 of the right 202 and left 204 iliac branch portions, respectively. Complementary pairing of apexes is indicated by the shared numbers, wherein the right branch portion apexes are designated by (R) and the left branch portion apexes are designated by (L). Each of the portions may be formed from a continuous single length of wire. See FIG. 7.

Figure 6:
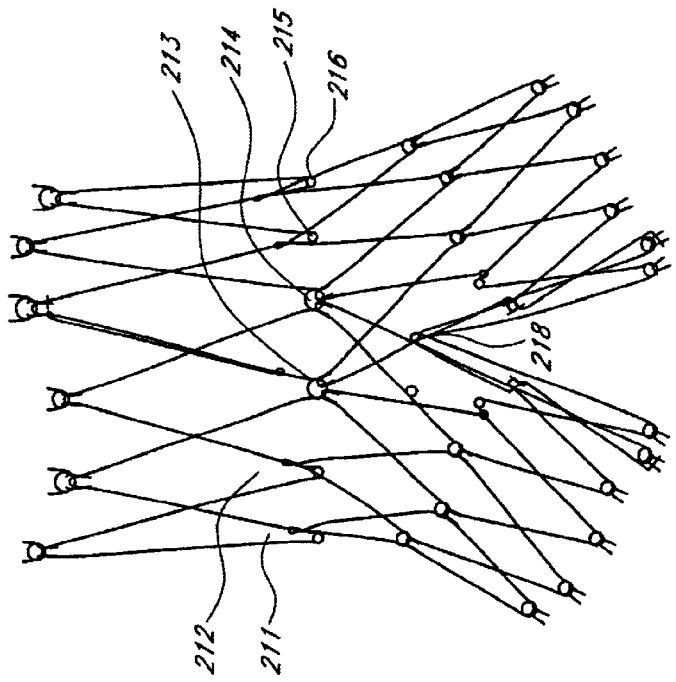
FIG. 6 is a schematic representation of the three-part wire support structure as in FIG. 5, illustrating the sliding articulation between the branch supports and the main body support.

Referring to FIG. 6, the assembled articulated wire support structure is shown. The central or medial apex 213 in the foreground (anterior) of the aortic trunk portion 200 is linked with 213(R) on the right iliac portion 202 and 213(L) on the left iliac portion 204. Similarly, the central apex 214 in the background (posterior) is linked with 214(R) on the right iliac portion 202 and 214(L) on the left iliac portion 204. Each of these linkages has two iliac apexes joined with one aortic branch apex. The medial most apexes 218 (R) and (L) of the iliac branch portions 202 and 204 are linked together, without direct connection with the aortic truck portion 200.

The medial apexes 213 and 214 function as pivot points about which the right and left iliac branches 202, 204 can pivot to accommodate unique anatomies. Although the right and left iliac branches 202, 204 are illustrated at an angle of about 45° to each other, they are articulable through at least an angle of about 90° and preferably at least about 120°. The illustrated embodiment allows articulation through about 180° while maintaining patency of the central lumen. To further improve patency at high iliac angles, the apexes 213 and 214 can be displaced proximally from the transverse plane which roughly contains apexes 211, 212, 215 and 216 by a minor adjustment to the fixture about which the wire is formed. Advancing the pivot point proximally relative to the lateral apexes (e.g., 211, 216) opens the unbiased angle between the iliac branches 202 and 204.

In the illustrated embodiment, the pivot point is formed by a moveable link between an eye on apex 213 and two apexes 213R and 213L folded therethrough. To accommodate the two iliac apexes 213R and 213L, the diameter of the eye at apex 213 may be slightly larger than the diameter of the eye on other apexes throughout the graft. Thus, for example, the diameter of the eye at apex 213 in one embodiment made from 0.014" diameter wire is about 0.059", compared to a diameter of about 0.020" for eyes elsewhere in the graft.

Although the pivot points (apexes 213, 214) in the illustrated embodiment are on the medial plane, they may be moved laterally such as, for example, to the axis of each of the iliac branches. In this variation, each iliac branch will have an anterior and a posterior pivot link on or about its longitudinal axis, for a total of four unique pivot links at the bifurcation. Alternatively, the pivot points can be moved as far as to lateral apexes 211 and 216. Other variations will be apparent to those of skill in the art in view of the disclosure herein.

To facilitate lateral rotation of the iliac branches 202, 204 about the pivot points and away from the longitudinal axis of the aorta trunk portion 200 of the graft, the remaining links between the aorta trunk portion 200 and the iliac branches 202, 204 preferably permit axial compression and expansion. In general, at least one and preferably several links lateral to the pivot point in the illustrated embodiment permit axial compression or shortening of the graft to accommodate lateral pivoting of the iliac branch. If the pivot point is moved laterally from the longitudinal axis of the aorta portion of the graft, any links medial of the pivot point preferably permit axial elongation to accommodate lateral rotation of the branch. In this manner, the desired range of rotation of the iliac branches may be accomplished with minimal deformation of the wire, and with patency of the graft optimized throughout the angular range of motion.

To permit axial compression substantially without deformation of the wire, the lateral linkages, 211 and 212 for the right iliac, and 215 and 216 for the left iliac, may be different from the previously described apex-to-apex linkage configurations. The lateral linkages are preferably slideable linkages, wherein a loop formed at the distal end of the iliac apex slidably engages a strut of the corresponding aortic truck portion. The loop and strut orientation may be reversed, as will be apparent to those of skill in the art. Interlocking "elbows" without any distinct loop may also be used. Such an axially compressible linkage on the lateral margins of the assembled wire support structure allow the iliac branch portions much greater lateral flexibility, thereby facilitating placement in patients who often exhibit a variety of iliac branch asymmetries and different angles of divergence from the aortic trunk.

Referring to FIG. 7, there is illustrated a plan view of a single formed wire used for rolling about a longitudinal axis to produce a four segment straight tubular wire support for an iliac limb. The formed wire exhibits distinct segments, each corresponding to an individual tubular segment in the tubular supports 202 or 204 (See FIG. 5). The distal segment I, is adapted to articulate with the aortic trunk portion 200 and the adjacent iliac limb portion. The distal segment (I) has two apexes (e.g. corresponding to 211 and 212 on the right iliac portion 202 in FIG. 5) which form a loop adapted to slidably engage a strut in the lateral wall of the aortic portion. These articulating loops (A) are enlarged in FIG. 8A. As discussed above, the loops are preferably looped around a strut on the corresponding apex of the proximal aortic segment to provide a sliding linkage.

The apex 218 is proximally displaced relative to the other four apexes in the distal segment (I). Apex 218 (R or L) is designed to link with the complementary 218 apex on the other iliac branch portion (See FIG. 6). The apex 218 in the illustrated embodiment is formed adjacent or near an intersegment connector 66, which extends proximally from the distal segment.

The other apexes on the distal segment (I) of an iliac limb are designed to link with a loop on the corresponding apex of the proximal aortic segment. Because many variations of this linkage are consistent with the present invention the form of the corresponding apexes may vary. In a preferred variation, the apexes (B) form a narrow U-shape, having an inside diameter of about 0.019 inches in an embodiment made from 0.012 inch Conichrome wire (tensile strength 300 ksi minimum) as illustrated in FIG. 8B. The U-shaped, elongated axial portion of the apex shown in FIG. 8B permits the apex to be wrapped through and around a corresponding loop apex of the proximal aortic segment.

In more general terms, the wire support illustrated in FIGS. 5 and 6 comprises a main body support structure formed from one or more lengths of wire and having a proximal end, a distal end and a central lumen extending along a longitudinal axis. The wire support also comprises a first branch support structure formed from one or more lengths of wire and having a proximal end, a distal end and a central lumen therethrough. The first branch support structure is pivotably connected to the proximal end of the main body support structure. The tubular wire support further comprises a second branch support structure formed from one or more lengths of wire and having a proximal end, a distal end and a central lumen extending therethrough. The distal end of the second branch support structure is pivotably connected to the proximal end of the main body support structure.

Further, the distal ends of the first and second branch structures may be joined together by a flexible linkage, formed for example between apexes 218(R) and 218(L) in FIG. 5. By incorporating a medial linkage between the two branch support structures and pivotable linkages with the main trunk, the first and second branch support structures can hinge laterally outward from the longitudinal axis without compromising the volume of the lumen. Thus, the branches may enjoy a wide range of lateral movement, thereby accommodating a variety of patient and vessel heterogeneity. Additional corresponding apexes between the main trunk and each iliac branch may also be connected, or may be free floating within the outer polymeric sleeve. Axially compressible lateral linkages, discussed above and illustrated in FIG. 6, may optionally be added.

The proximal apexes (C) of the iliac limb portions are adapted to link with the distal apexes of the next segment. These proximal apexes preferably form loops, such as those illustrated in FIG. 8C, wherein the elongated axial portions of the corresponding proximal apex in the adjacent segment can wrap around the loop, thereby providing flexibility of the graft.

The wire may be made from any of a variety of different alloys and wire diameters or non-round cross-sections, as has been discussed. In one embodiment of the bifurcation graft, the wire gauge remains substantially constant throughout section A of the primary component 49 and steps down to a second, smaller cross-section throughout section B of primary component 108.

A wire diameter of approximately 0.018 inches may be useful in the aorta trunk portion of a graft having five segments each having 2.0 cm length per segment, each segment having six struts intended for use in the aorta, while a smaller diameter such as 0.012 inches might be useful for segments of the graft having 6 struts per segment intended for the iliac artery.

In one embodiment of the present invention, the wire diameter may be tapered throughout from the proximal to distal ends of the section A and/or section B portions of the primary component 108. Alternatively, the wire diameter may be tapered incremental or stepped down, or stepped up, depending on the radial strength requirements of each particular clinical application. In one embodiment, intended for the abdominal aortic artery, the wire has a cross-section of about 0.018 inches in the proximal zone 110 and the wire tapers down regularly or in one or more steps to a diameter of about 0.012 inches in the distal zone 112 of the graft 102. End point dimensions and rates of taper can be varied widely, within the spirit of the present invention, depending upon the desired clinical performance.

In general, in the tapered or stepped wire embodiments, the diameter of the wire in the iliac branches is no more than about 80% of the diameter of the wire in the aortic trunk. This permits increased flexibility of the graft in the region of the iliac branches, which has been determined by the present inventors to be clinically desirable.

The collapsed prosthesis in accordance with the present invention has a diameter in the range of about 2 mm to about 10 mm. Preferably, the maximum diameter of the collapsed prosthesis is in the range of about 3 mm to 6 mm (12 to 18 French). Some embodiments of the delivery catheter including the prosthesis will be in the range of from 18 to 20 or 21 French; other embodiments will be as low as 19 F, 16 F, 14 F, or smaller. After deployment, the expanded endoluminal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

The self expandable bifurcation graft of the present invention can be deployed at a treatment site in accordance with any of a variety of techniques as will be apparent to those of skill in the art. One such technique is disclosed in copending patent application Ser. No. 08/802,478 entitled Bifurcated Vascular Graft and Method and Apparatus for Deploying Same, filed Feb. 20, 1997, the disclosure of which is incorporated in its entirety herein by reference.

Figure 9:
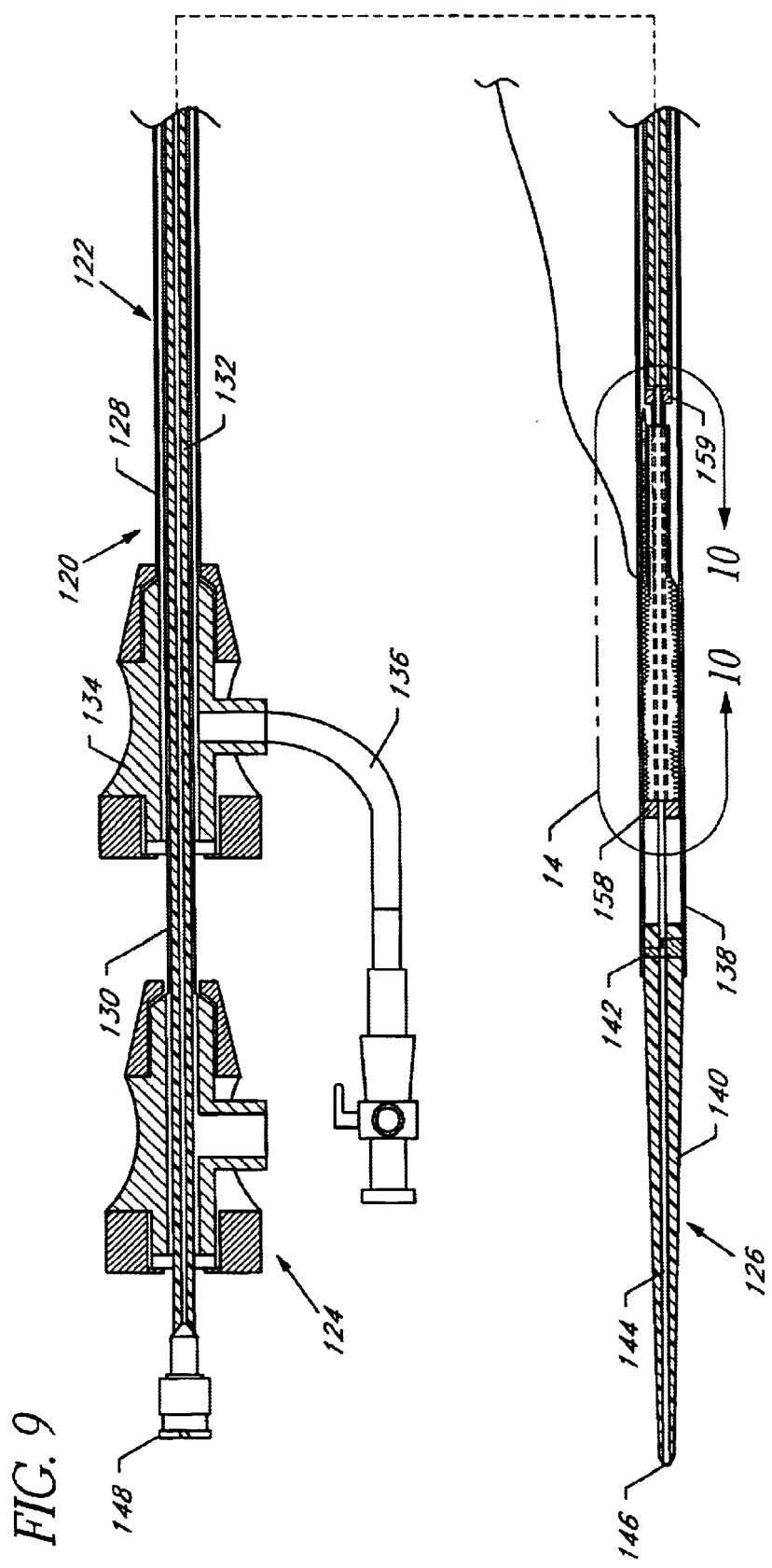
FIG. 9 is side elevational cross-section of a bifurcation graft delivery catheter in accordance with the present invention.

A partial cross-sectional side elevational view of one deployment apparatus 120 in accordance with the present invention is shown in FIG. 9. The deployment apparatus 120 comprises an elongate flexible multicomponent tubular body 122 having a proximal end 124 and a distal end 126. The tubular body 122 and other components of this system can be manufactured in accordance with any of a variety of techniques well known in the catheter manufacturing field. Suitable materials and dimensions can be readily selected taking into account the natural anatomical dimensions in the iliacs and aorta, together with the dimensions of the desired percutaneous access site.

The elongate flexible tubular body 122 comprises an outer sheath 128 which is axially movably positioned upon an intermediate tube 130. A central tubular core 132 is axially movably positioned within the intermediate tube 130. In one embodiment, the outer tubular sheath comprises extruded PTFE, having an outside diameter of about 0.250" and an inside diameter of about 0.230". The tubular sheath 128 is provided at its proximal end with a manifold 134, having a hemostatic valve 136 thereon and access ports such as for the infusion of drugs or contrast media as will be understood by those of skill in the art.

The outer tubular sheath 128 has an axial length within the range of from about 40" to about 55", and, in one embodiment of the deployment device 120 having an overall length of 110 cm, the axial length of the outer tubular sheath 128 is about 52 cm and the outside diameter is no more than about 0.250". Thus, the distal end 129 of the tubular sheath 128 is located at least about 16 cm proximally of the distal end 126 of the deployment catheter 120 in stent loaded configuration.

A distal segment of the deployment catheter 120 comprises an outer tubular housing 138, which terminates distally in an elongate flexible tapered distal tip 140. The distal housing 138 and tip 140 are axially immovably connected to the central core 132 at a connection 142.

In a preferred embodiment of the present invention, the central tubular core 132 is axially movably positioned within but rotationally locked to the intermediate tube 130. The intermediate tube 130 is preferably also axially movably positioned within but rotationally locked to the outer sheath 128. In this manner, the rotational orientation of the central tubular core 132 remains fixed with respect to the rotational orientation of the outer sheath 128.

Rotational engagement can be accomplished in any of a variety of ways, normally involving complementary surface structures such as keys or splines on the associated components. For example, the central tubular core 132 can be provided with a radially outwardly extending projection, along a portion or all of its axial length. This projection is slidably received within a radially outwardly extending slot on the interior surface of the intermediate tube 130, or component secured thereto. Alternatively, a radially inwardly extending projection on intermediate tube 130 or associated component can be received with an axially extending recess on the outer surface of the central tubular core 132. Alternatively, any of a variety of non-round configurations for the central tubular core 132 such as elliptical, oval, triangular, square, polygonal, and the like, can be slidably received within a complementary-shaped aperture on or connected to the intermediate tube 130.

In the illustrated embodiment, the cross section of the central tubular core 132 deviates from circular by the provision of one or two opposing flat sides extending axially along its length. A corresponding aperture is provided in a rotational lock 125 provided at the proximal end of the intermediate tube 130. See FIG. 9. Thus, rotation of the intermediate tube 130 will cause a similar rotation of the central tubular core 132.

Similarly, the intermediate tube 130 is provided with one or two opposing flat surfaces to be slidably received through a complementary aperture in a rotational lock 133 on manifold 134. See FIG. 9. The resulting assembly enables rotation of the manifold 134 to cause a commensurate rotation of the intermediate tube 130 and central tubular core 132. Specific dimensions and design details of the rotational lock disclosed herein will be readily apparent to those of skill in the art in view of the disclosure herein.

As can be seen from FIG. 10, a junction 131 is formed between the distal end 129 of outer sheath 128 and outer tubular housing 138. Proximal retraction of the outer sheath 128 with respect to the intermediate tube 130 and outer tubular housing 138 will expose the compressed iliac branches of the graft, as will be discussed in more detail below.

The distal tip 140 preferably tapers from an outside diameter of about 0.225" at its proximal end to an outside diameter of about 0.070" at the distal end thereof. The overall length of the distal tip 140 in one embodiment of the deployment catheter 120 is about 3". However, the length and rate of taper of the distal tip 140 can be varied depending upon the desired trackability and flexibility characteristics. The distal end of the housing 138 is secured to the proximal end of the distal tip 140 such as by thermal bonding, adhesive bonding, and/or any of a variety of other securing techniques known in the art. The proximal end of distal tip 140 is preferably also directly or indirectly connected to the central core 132 such as by a friction fit and/or adhesive bonding.

In at least the distal section of the catheter, the central core 132 preferably comprises a length of hypodermic needle tubing. The hypodermic needle tubing may extend throughout the length of the catheter to the proximal end thereof, or may be secured to the distal end of a proximal extrusion as illustrated for example in FIG. 6. A central guidewire lumen 144 extends throughout the length of the tubular central core 132, having a distal exit port 146 and a proximal access port 148 as will be understood by those of skill in the art.

Referring to FIGS. 10–12, a bifurcated endoluminal graft 150 is illustrated in a compressed configuration within the deployment catheter 120. The graft 150 comprises a distal aortic section 152, a proximal ipsilateral iliac portion 154, and a proximal contralateral iliac portion 156. The aortic trunk portion 152 of the graft 150 is contained within the tubular housing 138. Distal axial advancement of the central tubular core 132 will cause the distal tip 140 and housing 138 to advance distally with respect to the graft 150, thereby permitting the aortic trunk portion 152 of the graft 150 to expand to its larger, unconstrained diameter. Distal travel of the graft 150 is prevented by a distal stop 158 which is axially immovably connected to the intermediate tube 130. Distal stop 158 may comprise any of a variety of structures, such as an annular flange or component which is adhered to, bonded to or integrally formed with a tubular extension 160 of the intermediate tube 132. Tubular extension 160 is axially movably positioned over the hypotube central core 132.

The tubular extension 160 extends axially throughout the length of the graft 150. At the proximal end of the graft 150, a step 159 axially immovably connects the tubular extension 160 to the intermediate tube 130. In addition, the step 159 provides a proximal stop surface to prevent proximal travel of the graft 150 on the catheter 120. The function of step 159 can be accomplished through any of a variety of structures as will be apparent to those of skill in the art in view of the disclosure herein. For example, the step 159 may comprise an annular ring or spacer which receives the tubular extension 160 at a central aperture therethrough, and fits within the distal end of the intermediate tube 130. Alternatively, the intermediate tube 130 can be reduced in diameter through a generally conical section or shoulder to the diameter of tubular extension 160.

Proximal retraction of the outer sheath 128 will release the iliac branches 154 and 156 of the graft 150. The iliac branches 154 and 156 will remain compressed, within a first (ipsilateral) tubular sheath 162 and a second (contralateral) tubular sheath 164. The first tubular sheath 162 is configured to restrain the ipsilateral branch of the graft 150 in the constrained configuration, for implantation at the treatment site. The first tubular sheath 162 is adapted to be axially proximally removed from the iliac branch, thereby permitting the branch to expand to its implanted configuration. In one embodiment, the first tubular sheath 162 comprises a thin walled PTFE extrusion having an outside diameter of about 0.215" and an axial length of about 7.5 cm. A proximal end of the tubular sheath 162 is necked down such as by heat shrinking to secure the first tubular sheath 162 to the tubular extension 160. In this manner, proximal withdrawal of the intermediate tube 130 will in turn proximally advance the first tubular sheath 162 relative to the graft 150, thereby deploying the self expandable iliac branch of the graft 150.

The second tubular sheath 164 is secured to the contralateral guidewire 166, which extends outside of the tubular body 122 at a point 168, such as may be conveniently provided at the junction 131 between the outer tubular sheath 128 and the distal housing 138. The second tubular sheath 164 is adapted to restrain the contralateral branch of the graft 150 in the reduced profile. In one embodiment of the invention, the second tubular sheath 164 has an outside diameter of about 0.215" and an axial length of about 7.5 cm. The second tubular sheath 164 can have a significantly smaller cross-section than the first tubular sheath 162, due to the presence of the tubular core 132 and intermediate tube 130 within the first iliac branch 154.

The second tubular sheath 164 is secured at its proximal end to a distal end of the contralateral guidewire 166. This may be accomplished through any of a variety of securing techniques, such as heat shrinking, adhesives, mechanical interfit and the like. In one embodiment, the guidewire is provided with a knot or other diameter enlarging structure to provide an interference fit with the proximal end of the second tubular sheath 156, and the proximal end of the second tubular sheath 156 is heat shrunk and/or bonded in the area of the knot to provide a secure connection. Any of a variety of other techniques for providing a secure connection between the contralateral guidewire 166 and tubular sheath 156 can readily be used in the context of the present invention as will be apparent to those of skill in the art in view of the disclosure herein. The contralateral guidewire 166 can comprise any of a variety of structures, including polymeric monofilament materials, braided or woven materials, metal ribbon or wire, or conventional guidewires as are well known in the art.

Referring to FIGS. 13 and 14, there is illustrated a fragmentary side elevational view of an enhanced flexibility embodiment of the deployment catheter of the present invention. In this embodiment, the distal component 134 of the central tubular core 132 comprises a flexible wall such as a braided polyimide tubing. In one embodiment, the polyimide tubing has an inside diameter of about 0.059" and an outside diameter of about 0.071". An internal braid is made from 0.0015" stainless steel 304 wire at a pic count of about 50 braids per inch, such as may be obtained from Phelps Dodge (GA) or H.V. Technologies (GA). The use of flexible tubing such as spiral cut layers or woven or braided tubing in place of conventional stainless steel or other metal hypotubing increases the lateral flexibility of the assembled device, which facilitates the placement and deployment steps.

However, introduction of a flexible hypotube 134 creates a flex point in the catheter at about the junction 131 between the distal end 129 of outer sheath 128 and the proximal end of the outer tubular housing 138. To prevent kinking at the junction 131, a reinforcement structure 161 is preferably provided within the catheter, spanning the junction 131. In the illustrated embodiment, the reinforcement structure 161 is carried by the tubular extension 160 of intermediate tube 130. The reinforcement structure 161 is in the form of a tubular element such as a stainless steel hypotube. The illustrated hypotube has a length within the range of from about 40 mm to about 60 mm, a wall thickness within the range of from about 0.002" to about 0.005" and is secured immovably to the tubular extension 160. Any of a variety of other reinforcement structures 161 can also be used, such as spiral cut or woven or braided layers, polymeric tubing and the like, depending upon the desired performance characteristics. By positioning the reinforcement structure 161 at about the axial location of the junction 131, the flexibility characteristics of the catheter can be optimized, while permitting a highly flexible hypotube 134.

The dimensions of the reinforcement tube 161 can be varied, depending upon the desired performance characteristics of the catheter. For example, in the embodiment illustrated in part in FIG. 13A, the reinforcement tube extends proximally at least as far as the proximal stop 159 which will be discussed. The reinforcement tube 161 may also extend distally as far as the distal stop 158. In the embodiment illustrated in FIG. 13A, the reinforcement tube 161 extends distally beyond the proximal stop 159 for a length of about 4.8 inches. The reinforcing sleeve has an inside diameter of about 0.072 inches and an outside diameter of about 0.076 inches. Other dimensions may be utilized, depending upon the desired balance between flexibility and kink resistance, as well as other performance characteristics. See, e.g., FIG. 13.

The braided polyimide hypotube 134, or other braided or woven reinforced tubular element can be secured to the enlarged diameter proximal component 134 of tubular core 132 (see FIG. 14) in any of a variety of ways. In the illustrated embodiment, a threaded insert 163 is adhesively bonded to the polyimide hypotube component 134 of the tubular core 132 using a flexible epoxy such as 310 T manufactured by Epotech (MASS.) or other adhesives known in the art.

Figure 13A:
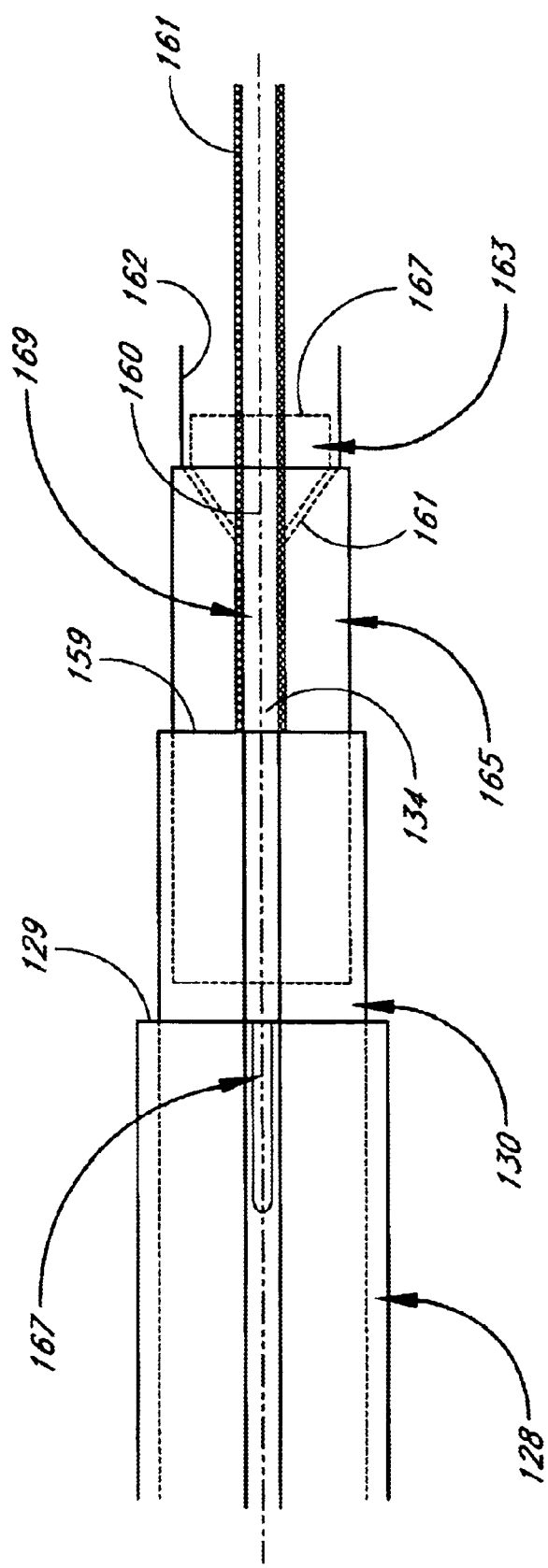
FIG. 13A is a fragmentary side elevational view of a further feature of the deployment catheter in accordance with the present invention.

A further optional feature of the deployment system in accordance with the present invention is illustrated in FIG. 13A. In this simplified fragmentary view, the distal end of the intermediate tube 130 is illustrated as extending out of the distal end 129 of the outer sheath 128. A slit 167 is illustrated in the outer sheath, to accommodate the contralateral guidewire 166. The distal end of the intermediate tube 130 is provided with a proximal stop 159, for supporting the graft as has been discussed and for connecting the tubular extension 160 to the intermediate tube 130. The tubular extension 160 extends distally and supports the proximal end 165 of the ipsilateral tubular sheath 162.

In this embodiment, the proximal end 165 of ipsilateral tubular sheath 162 is tapered such as by necking down the outside diameter of the ipsilateral tubular sheath 162 for bonding to the tubular extension 160. This creates a generally conical space within the end of the tubular sheath 162, which can potentially collapse and cause binding upon distal advance of the outer sheath 128. Thus, a plug 163 having a generally conical shape may be provided to fill the proximal end 165 of the ipsilateral tubular sheath 162, thereby presenting a surface 167 for facing the graft (not illustrated). The plug 163 may be manufactured in any of a variety of ways, such as by injection molding or machining, or by introducing a curable or otherwise hardenable agent into the proximal end 165 and curing it in place to provide a surface 167.

Another optional feature of the deployment catheter is a spacer 171. In the embodiment illustrated in FIG. 10, for example, it can be seen that the outside diameter of the ipsilateral tubular sheath 162 tapers down to approximately the inside diameter of the tubular extension 160, which is considerably smaller than the outside diameter of the intermediate tube 130. This low diameter space between the ipsilateral tubular sheath 162 and intermediate tube 130 creates an opportunity for the distal end of the outer sheath 128 to become engaged (snagged) with the proximal end 165 of sheath 162 as the outer sheath 128 is advanced distally along the deployment device. This may occur, for example, after the outer sheath 128 has been proximally retracted to release the contralateral graft, and thereafter distally advanced to support the ipsilateral graft during deployment of the contralateral graft.

To prevent the distal edge 129 of the outer sheath 128 from snagging on the proximal end 165 of the sheath 162, a spacer 171 is preferably positioned to fill the space between the stop 159 and the sheath 162. The spacer 171 may be a solid component, such as a molded or machined part, or a tubular element such as an extrusion. In one embodiment, as illustrated in FIG. 13A, the spacer 171 comprises a molded tubular element having a diameter of about 0.185", a total axial length of about 0.153", and a length of about 0.74" from 159 to the distal end of 171. A slot or recess 169 is provided for receiving the joint between the proximal end of the contralateral branch and the contralateral guidewire 166. The spacer 171 may be assembled as a separately manufactured component, or may be integrally formed with either the stop 159, the intermediate tube 130 or the sheath 162.

In use, the free end of the contralateral guidewire 166 is percutaneously inserted into the arterial system, such as at a first puncture in a femoral artery. The contralateral guidewire is advanced through the corresponding iliac towards the aorta, and crossed over into the contralateral iliac in accordance with cross over techniques which are well known in the art. The contralateral guidewire is then advanced distally down the contralateral iliac where it exits the body at a second percutaneous puncture site.

The deployment catheter 120 is thereafter percutaneously inserted into the first puncture, and advanced along a guidewire (e.g. 0.035 inch) through the ipsilateral iliac and into the aorta. As the deployment catheter 120 is transluminally advanced, slack produced in the contralateral guidewire 166 is taken up by proximally withdrawing the guidewire 166 from the second percutaneous access site. In this manner, the deployment catheter 120 is positioned in the manner generally illustrated in FIG. 13. Referring to FIG. 14, the outer sheath 128 is proximally withdrawn while maintaining the axial position of the overall deployment catheter 120, thereby releasing the first and second iliac branches of the graft 150. Proximal advancement of the deployment catheter 120 and contralateral guidewire 166 can then be accomplished, to position the iliac branches of the graft 150 within the iliac arteries as illustrated.

Figure 15:
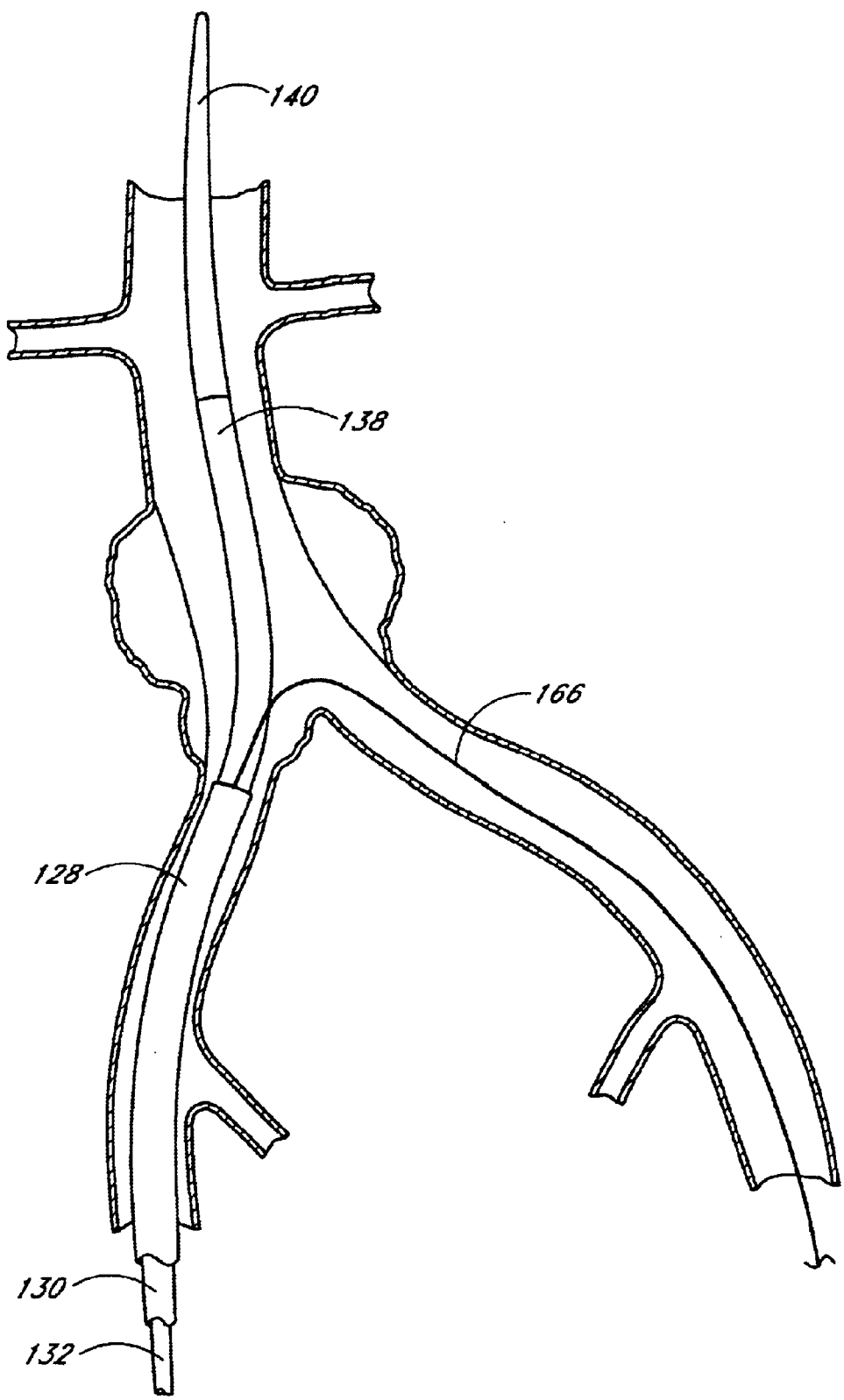
FIG. 15 is a schematic representation of a bifurcated graft deployment catheter of the present invention, positioned within the ipsilateral iliac and the aorta, with the contralateral guidewire positioned within the contralateral iliac.
Figure 16:
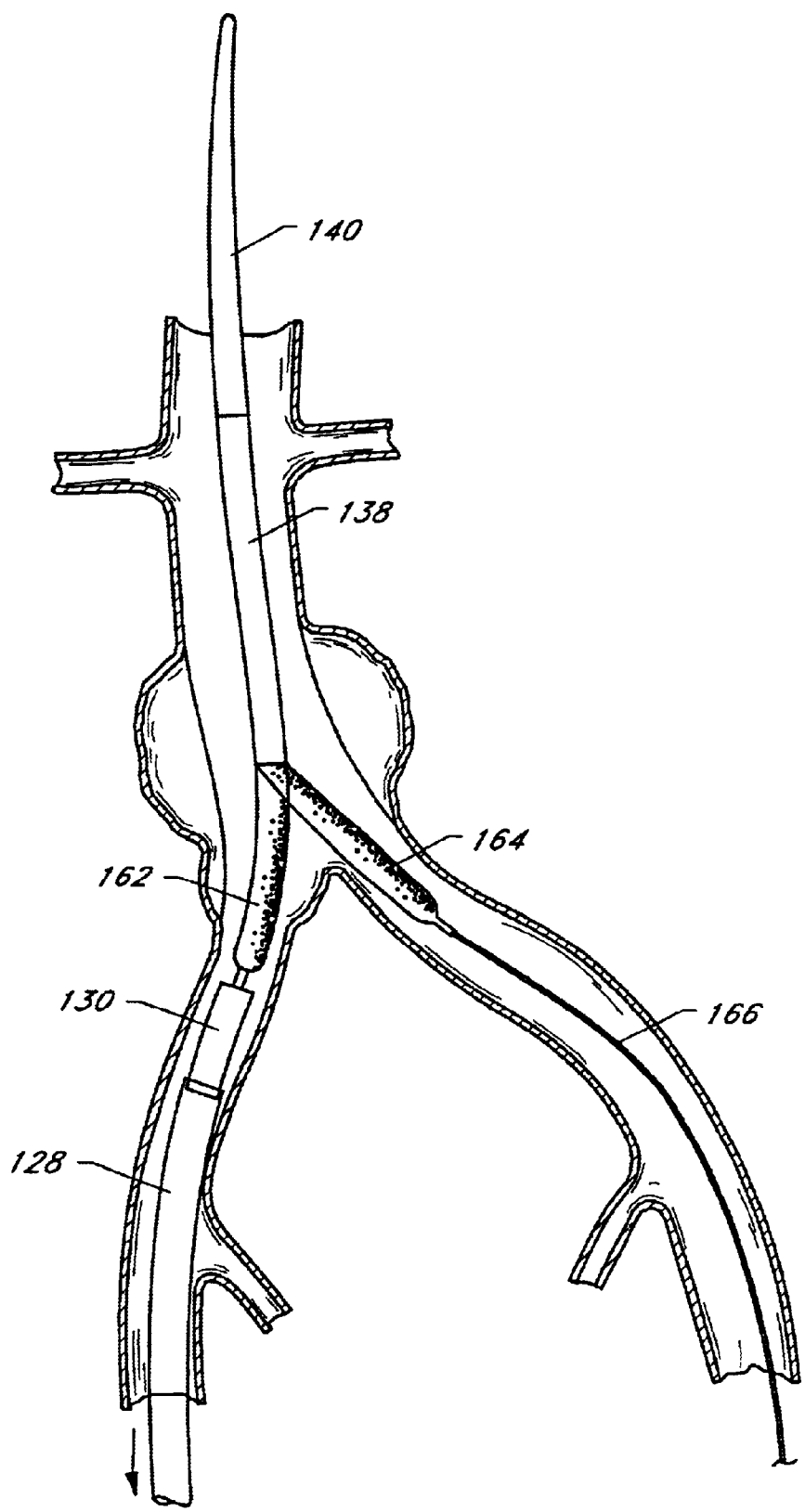
FIG. 16 is a schematic representation as in FIG. 15, with the outer sheath proximally retracted and the compressed iliac branches of the graft moving into position within the iliac arteries.

Referring to FIG. 15, the central core 132 is distally advanced thereby distally advancing the distal housing 138 as has been discussed. This exposes the aortic trunk of the graft 150, which deploys into its fully expanded configuration within the aorta. As illustrated in FIG. 16, the contralateral guidewire 166 is thereafter proximally withdrawn, thereby by proximally withdrawing the second sheath 164 from the contralateral iliac branch 156 of the graft 150. This may be preceded by the step of distally advancing the outer sheath 128 up to the bifurcation to provide support while the second sheath 164 is removed. The contralateral branch 156 of the graft 150 thereafter self expands to fit within the iliac artery. The guidewire 166 and sheath 164 may thereafter be proximally withdrawn and removed from the patient, by way of the second percutaneous access site.

Figure 17:
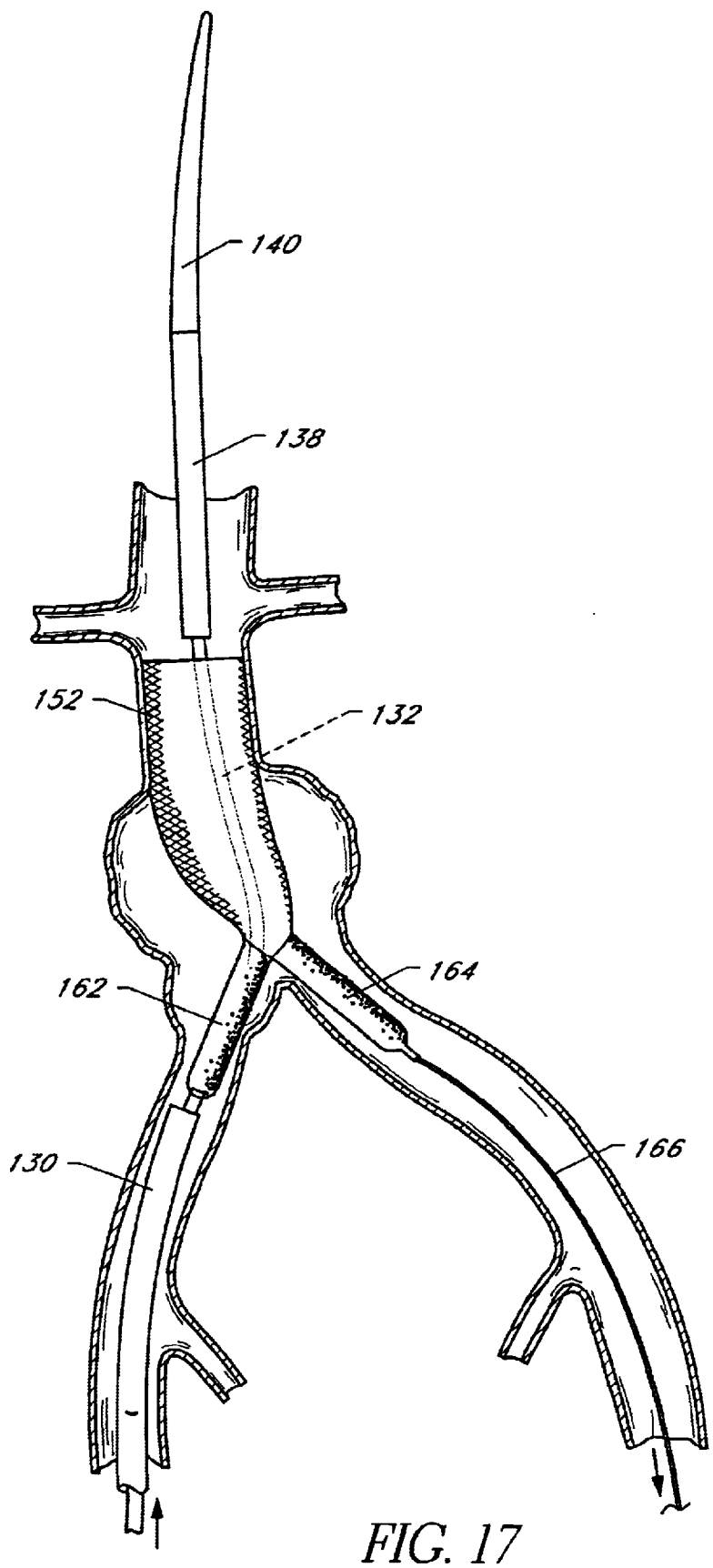
FIG. 17 is a schematic representation as in FIG. 16, with the compressed iliac branches of the graft within the iliac arteries, and the main aortic trunk of the graft deployed within the aorta.
Figure 18:
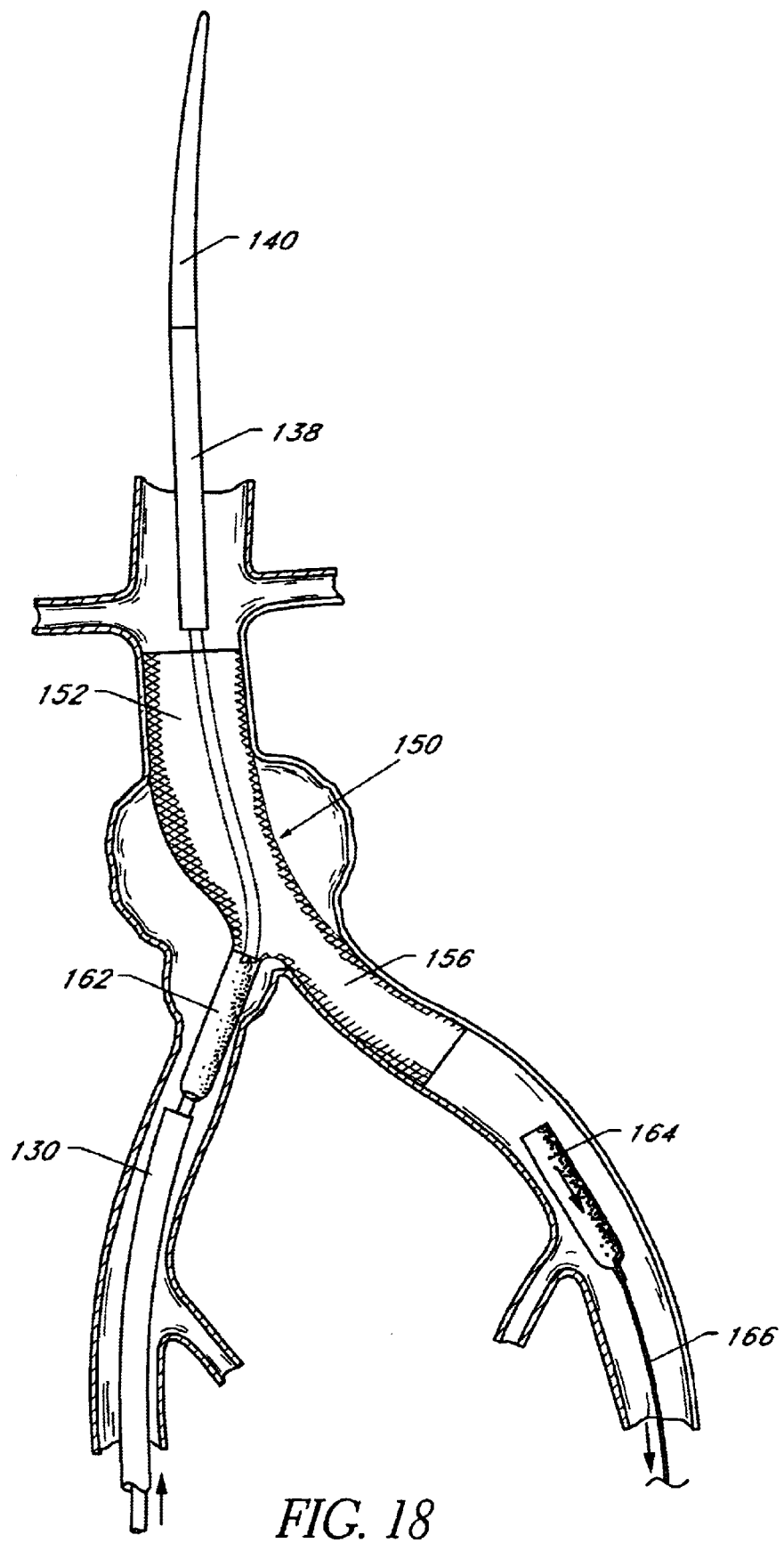
FIG. 18 is a schematic representation as in FIG. 17, with the contralateral iliac branch of the graft deployed.
Figure 19:
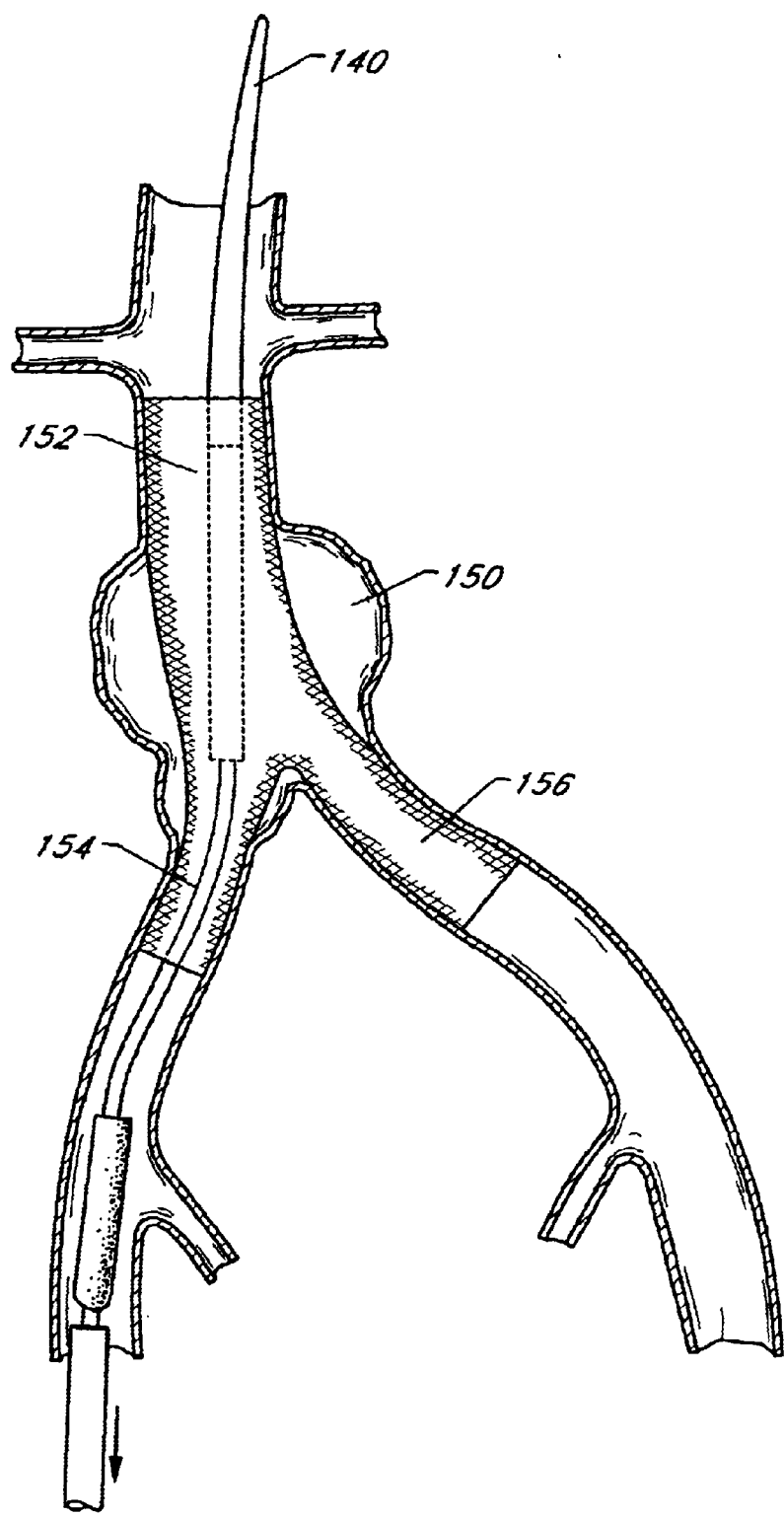
FIG. 19 is a schematic representation as in FIG. 18, following deployment of the ipsilateral branch of the graft.

Thereafter, the deployment catheter 120 may be proximally withdrawn to release the ipsilateral branch 154 of the graft 150 from the first tubular sheath 162 as shown in FIG. 17. Following deployment of the ipsilateral branch 154 of the prosthesis 150, a central lumen through the aortic trunk 152 and ipsilateral branch 154 is sufficiently large to permit proximal retraction of the deployment catheter 120 through the deployed bifurcated graft 150. The deployment catheter 120 may thereafter be proximally withdrawn from the patient by way of the first percutaneous access site.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. An endoluminal graft deployment catheter, comprising:
   a proximal outer tube section, having a proximal end and a distal end; an intermediate tube extending through the proximal tube section and beyond the distal end;
   a central core, extending through the intermediate tube; and
   a cap attached to the central core;
   a tubular sheath having an open distal end and a proximal end, the open distal end of the sheath having a first diameter and the proximal end of the tubular sheath having a second diameter that is smaller than the first diameter at the proximal end to form a generally conical section of the proximal cavity for receiving the proximal end of a prosthesis, the proximal end of the sheath being coupled to the intermediate tube; and
   a generally conical plug positioned in the generally conical section of the proximal cavity, the plug defining a distal surface that faces a proximal end of the prosthesis.
   a tubular sheath having an open distal end and a proximal end, the open distal end of the tubular sheath having a first diameter and the proximal end of the tubular sheath having a second diameter that is smaller than the first diameter to form a generally conical section of the proximal cavity for receiving the proximal end of a prosthesis, the proximal end of the tubular sheath being coupled to the second portion of the intermediate tube; and
   a generally conical plug positioned in the generally conical section of the proximal cavity, the plug defining a distal surface that faces a proximal end of the prosthesis; and
   a spacer for filling at least partially a space between the distally facing surface of the intermediate tube and an outer surface of the tubular sheath
   wherein the proximal and distal tube sections define a prosthesis cavity therein for carrying the prosthesis; and axial separation of the proximal tube section from the distal tube section opens the cavity to release the prosthesis.

2. An endoluminal graft deployment catheter as in claim 1, wherein the intermediate tube is rotationally linked to the outer tube.

3. An endoluminal graft deployment catheter as in claim 1, wherein the cap is axially movable between a first position in which it contacts the outer tube and a second position in which it is spaced distally apart from the outer tube.

4. An endoluminal graft deployment catheter as in claim 3, wherein the central core comprises a flexible tube.

5. An endoluminal graft deployment catheter as in claim 4, wherein the tube comprises a polymeric braid.

6. An endoluminal graft deployment catheter as in claim 5, wherein the tube further comprises a reinforcing element which overlaps the point of contact between the cap and the outer tube.

7. An endoluminal graft deployment catheter as in claim 6, wherein the reinforcing element comprises a tubular element carried by the flexible tube.

8. An endoluminal graft deployment catheter as in claim 1, wherein the plug has a generally conical shape, and the distal surface is on a larger diameter end of the plug.

9. An endoluminal graft deployment catheter, comprising:
   an elongate flexible body, having a proximal end and a distal end;
   a proximal outer tube section, having a proximal end and a distal end;
   a distal outer tube section, having a proximal end and a distal end,
   an intermediate tube extending through the proximal outer sheath tube section and beyond the distal end; the intermediate tube having a first portion and a second portion. the first portion having a larger diameter than the second portion to form a distally facing surface;
   a central core, extending through the proximal and distal outer tube sections and the intermediate tube.

10. An endoluminal graft deployment catheter as in claim 9, wherein each of the proximal tube section and the distal tube section is rotationally linked to the central core.

11. An endoluminal graft deployment catheter as in claim 9, wherein at least one of the proximal tube section and the distal tube section is axially movable between a first position in which the cavity is closed and a second position in which the cavity is open.

12. An endoluminal graft deployment catheter as in claim 11, comprising a junction between the proximal tube section and the distal tube section when the cavity is closed, and further comprising a reinforcing element spanning the junction.

13. An endoluminal graft deployment catheter as in claim 12, wherein the reinforcing element comprises a tube.

14. An endoluminal graft deployment catheter, comprising:

an elongate, flexible body, having a proximal end and a distal end;

a proximal outer tube section having a proximal end and a distal end;

a distal outer tube section, having a proximal end and a distal end;

an intermediate tube extending through the proximal outer sheath tube section and beyond the distal end:

a central core, extending between the proximal outer tube section and the distal outer tube section and the intermediate tube, wherein at least one of the proximal outer tube section and the distal outer tube section is axially moveable between a first position in which the proximal outer tube section and the distal outer tube section are adjacent each other, and a second position in which the proximal outer tube section and the distal outer tube section are spaced apart, the outer tube section and the distal outer tube section forming a junction when in the first position; and a tubular sheath having an open distal end and a proximal end, the tubular sheath defining proximal cavity for receiving a proximal end of a prosthesis, the tubular sheath necking down from a first larger diameter to a second smaller diameter at the proximal end to form a generally conical section of the proximal cavity, and a generally conical plug positioned in the generally conical section of the proximal cavity, the plug defining a distal surface that faces a proximal end of the prosthesis.

15. An endoluminal graft deployment catheter as in claim 14, wherein the tubular sheath is necked down at the proximal end by heat shrinking.

16. An endoluminal graft deployment catheter as in claim 14, the intermediate tube has a first portion and a second portion, the first portion having a larger diameter than the second, portion to form a distally facing surface.

17. An endoluminal graft deployment catheter as in claim 13, comprising a spacer for filling at least partially a space between the distally facing surface of the intermediate tube and an outer surface of the tubular sheath.

* * * * *